US010912926B2

(12) United States Patent
Bailey et al.

(10) Patent No.: US 10,912,926 B2
(45) Date of Patent: Feb. 9, 2021

(54) PERIPHERALLY INSERTED CENTRAL CATHETER SYSTEMS, DEVICES, AND METHODS THEREOF FOR PEDIATRICS

(71) Applicant: C. R. Bard, Inc., Murray Hill, NJ (US)

(72) Inventors: Lisa I. Bailey, Millcreek, UT (US); Chad A. Hadley, North Salt Lake, UT (US); Caleb Campbell, Clearfield, UT (US); Paul H. Shin, Salt Lake City, UT (US); Richard B. Lewis, Novato, CA (US)

(73) Assignee: C. R. Bard, Inc., Franklin Lakes, NJ (US)

(*) Notice: Subject to any disclaimer, the term of this patent is extended or adjusted under 35 U.S.C. 154(b) by 253 days.

(21) Appl. No.: 15/594,021

(22) Filed: May 12, 2017

(65) Prior Publication Data

US 2017/0326339 A1 Nov. 16, 2017

Related U.S. Application Data

(60) Provisional application No. 62/336,557, filed on May 13, 2016.

(51) Int. Cl.
*A61M 25/02* (2006.01)
*A61M 25/01* (2006.01)
(Continued)

(52) U.S. Cl.
CPC ........ *A61M 25/02* (2013.01); *A61M 25/0021* (2013.01); *A61M 25/0023* (2013.01);
(Continued)

(58) Field of Classification Search
CPC .. A61M 25/02; A61M 25/0021; A61M 25/01; A61M 25/0637; A61M 25/0023;
(Continued)

(56) References Cited

U.S. PATENT DOCUMENTS 8,439,873 B1 * 5/2013 Donovan ............... A61M 25/00
604/116
8,603,070 B1 * 12/2013 Lareau .................. A61L 29/049
604/529

(Continued)

OTHER PUBLICATIONS

Wilder, N. S., et al. "Fluid Overload is Associated with Late Poor Outcomes in Neonates Following Cardiac Surgery" Pediatr. Crit. Care Med.; 17(5): 420-427. doi:10.1097/PCC.0000000000000715. (May 2016).

*Primary Examiner* — Lauren P Farrar
(74) *Attorney, Agent, or Firm* — Rutan & Tucker LLP

(57) ABSTRACT

A catheterization system for treatment of patients can include a peripherally inserted central catheter comprising a catheter tube joined to an extension leg with a junction and a securement device that fits around a portion of the junction to inhibit movement. The catheter tube can include a taper proximate the junction, the taper transitioning the catheter tube from a larger outer diameter and a larger wall thickness to a smaller outer diameter and a smaller wall thickness. The taper and thicker wall thickness near the junction can help prevent damage to the catheter tube near the junction when bent (e.g., to secure a proximal region of the catheter to a patient's arm). The securement device can configured to fit around an outer diameter of the junction to inhibit movement of the junction when the junction is held in the securement device.

24 Claims, 21 Drawing Sheets

(51) Int. Cl.
   *A61M 25/00* (2006.01)
   *A61M 25/06* (2006.01)
   *A61M 39/00* (2006.01)

(52) U.S. Cl.
   CPC ........ *A61M 25/01* (2013.01); *A61M 25/0637* (2013.01); *A61M 25/0032* (2013.01); *A61M 39/00* (2013.01); *A61M 2025/0008* (2013.01); *A61M 2025/024* (2013.01); *A61M 2025/0266* (2013.01); *A61M 2039/0036* (2013.01); *A61M 2039/0054* (2013.01); *A61M 2240/00* (2013.01)

(58) Field of Classification Search
   CPC ...... A61M 25/0032; A61M 2039/0036; A61M 2025/0266; A61M 2025/0008; A61M 2025/024; A61M 39/00; A61M 2039/0054; A61M 2240/00
   See application file for complete search history.

(56) References Cited

U.S. PATENT DOCUMENTS

| | | | |
|---|---|---|---|
| 2005/0226855 A1* | 10/2005 | Alt | A61M 25/0023 424/93.7 |
| 2006/0206094 A1* | 9/2006 | Chesnin | A61M 25/0021 604/508 |
| 2007/0049999 A1* | 3/2007 | Esch | A61B 18/08 607/96 |
| 2007/0265572 A1* | 11/2007 | Smith | A61M 25/02 604/174 |
| 2009/0143740 A1* | 6/2009 | Bierman | A61M 5/1415 604/177 |
| 2012/0041377 A1* | 2/2012 | Haak | A61M 25/02 604/180 |
| 2016/0193453 A1* | 7/2016 | Isaacson | A61M 25/0625 604/263 |
| 2016/0213887 A1* | 7/2016 | Jacovini | A61M 1/0086 |
| 2016/0325074 A1* | 11/2016 | Lareau | A61M 25/0023 |

* cited by examiner

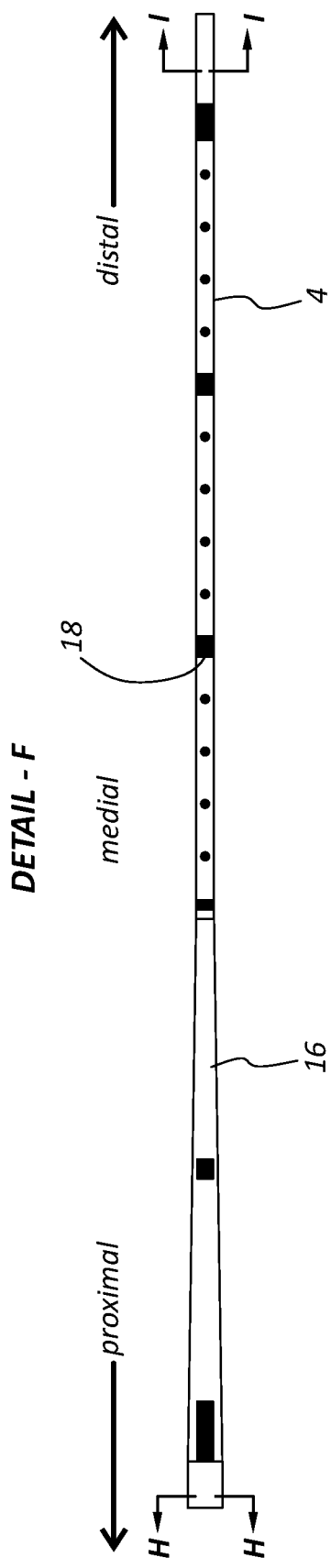
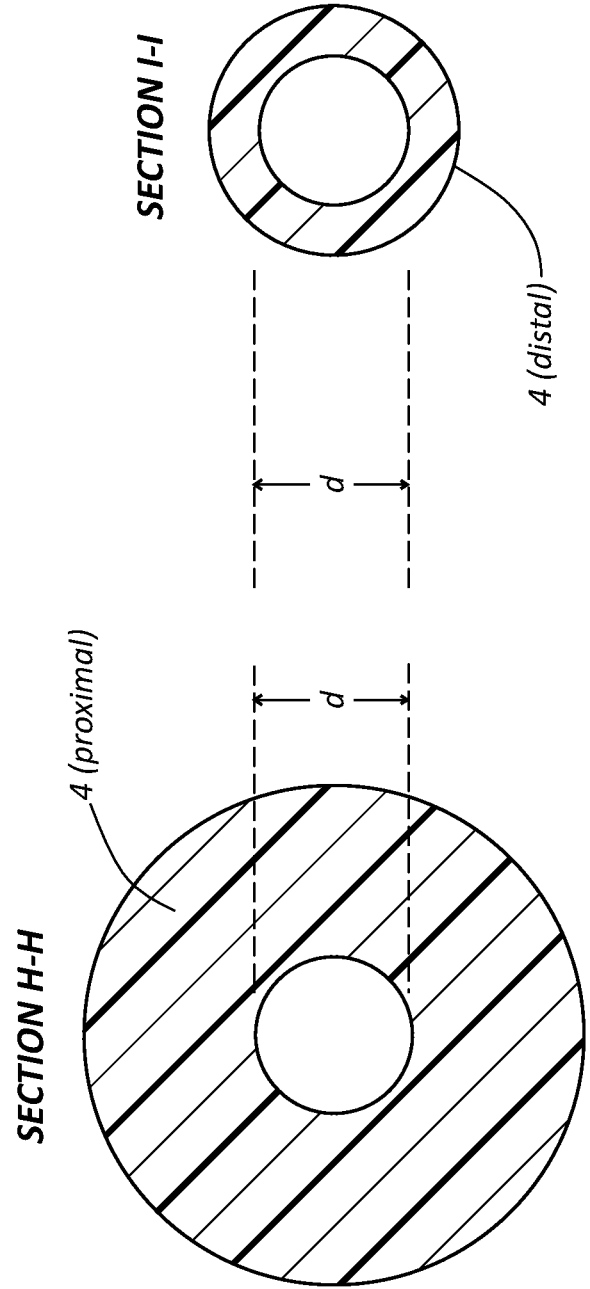

DETAIL - A

DETAIL - G

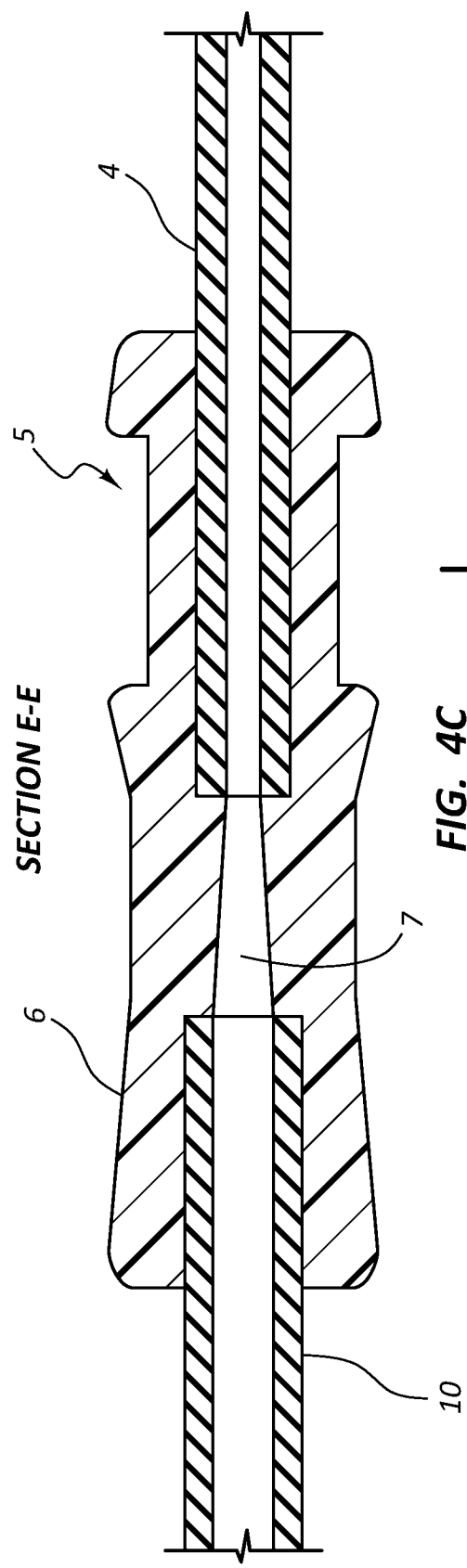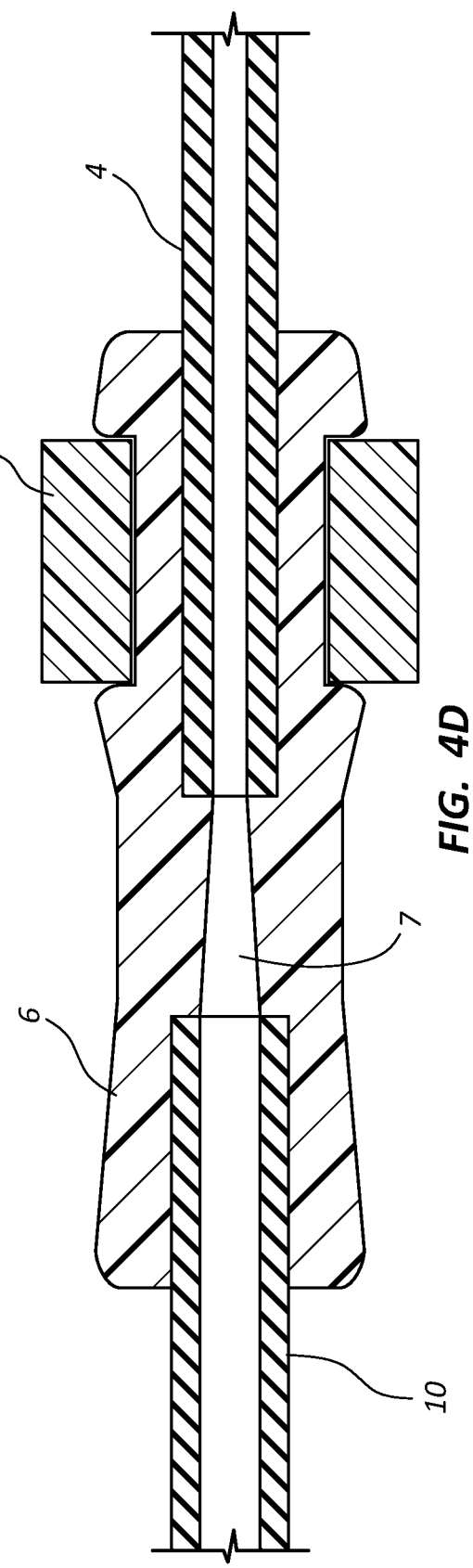

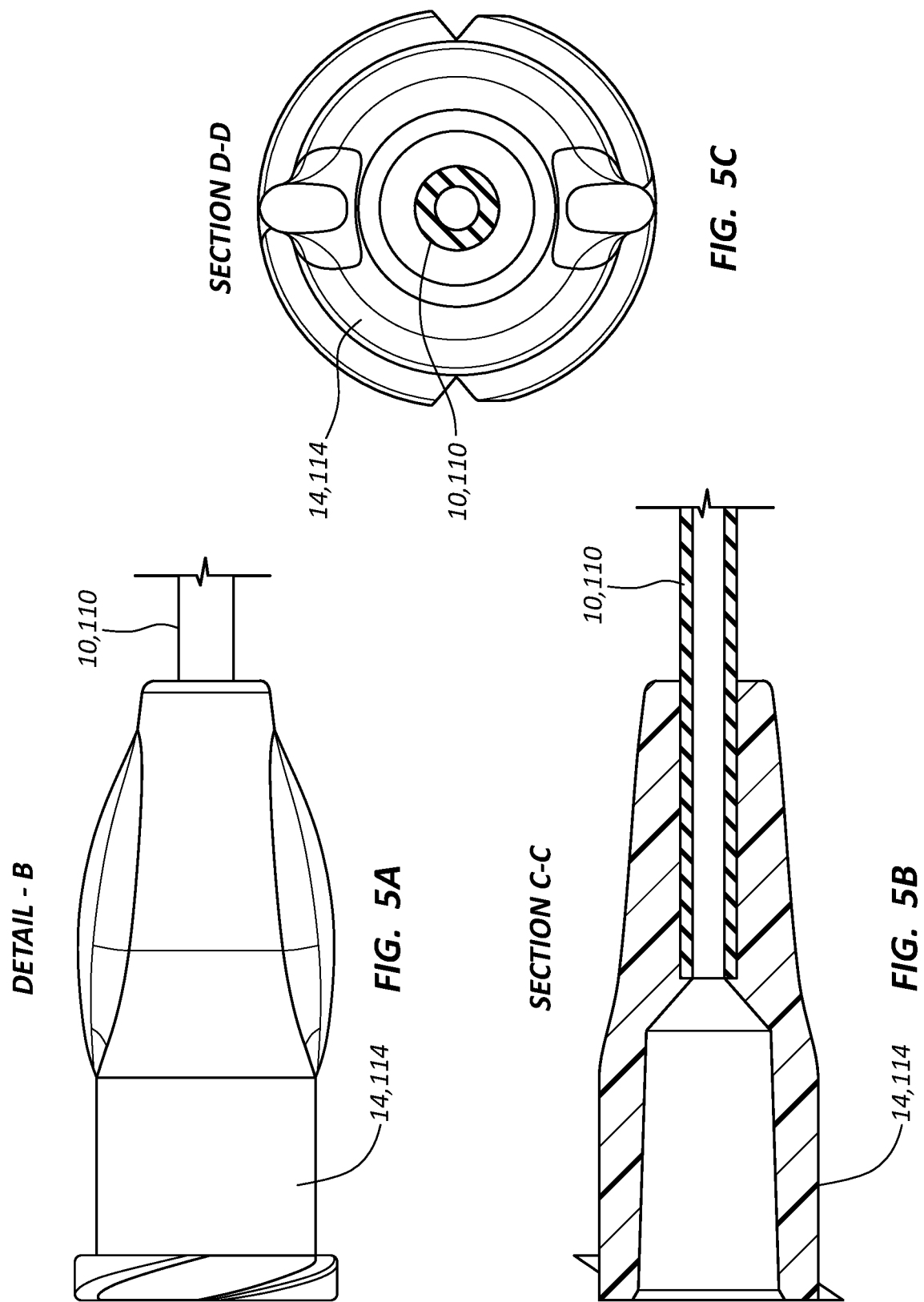

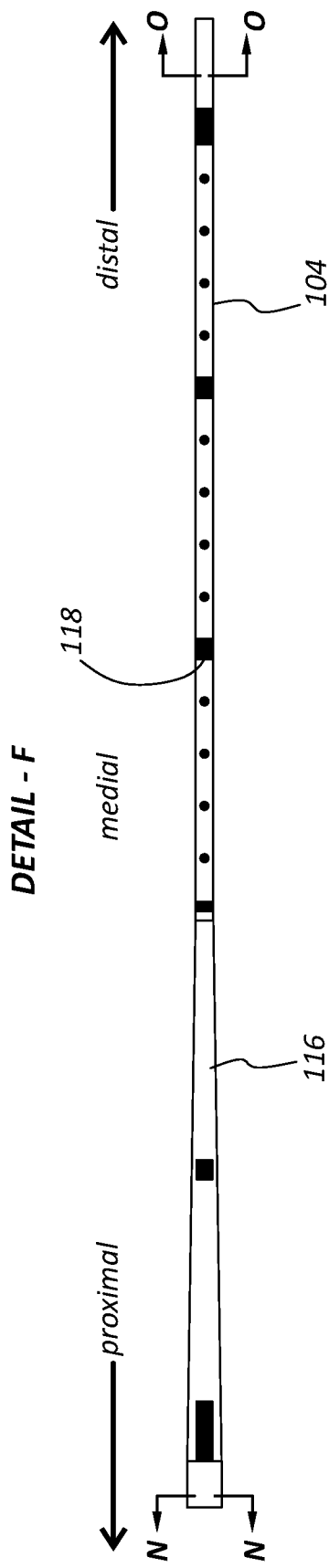
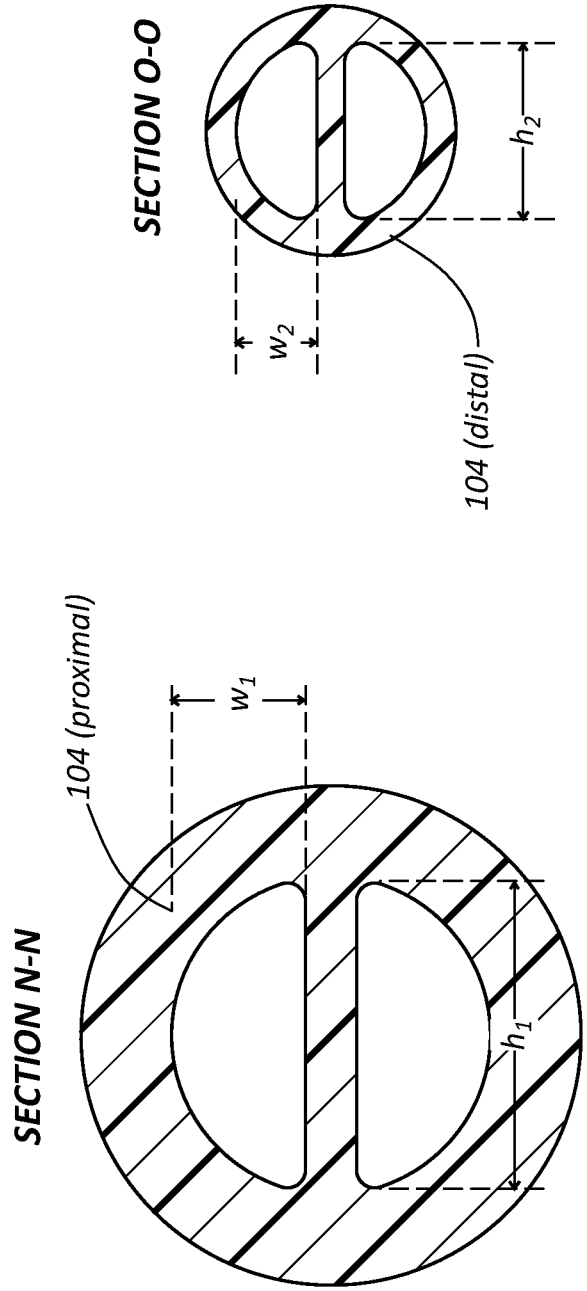
FIG. 8A
FIG. 8B
FIG. 8C

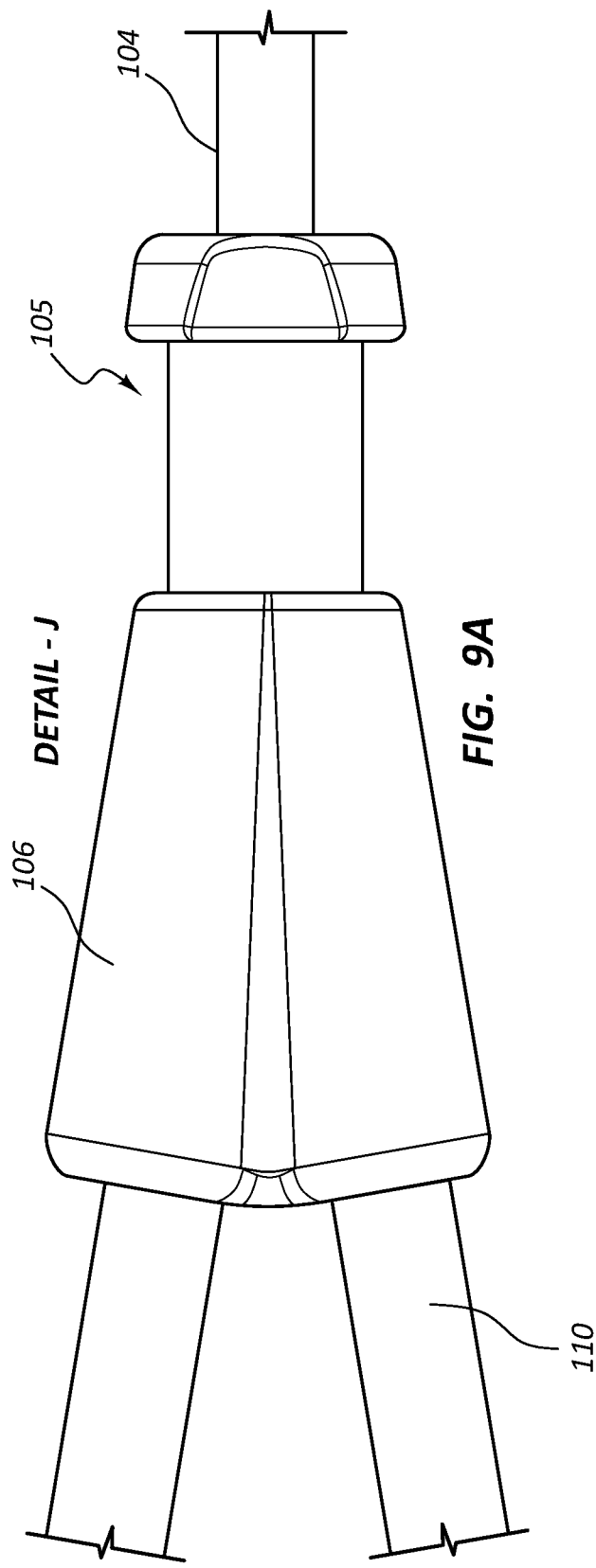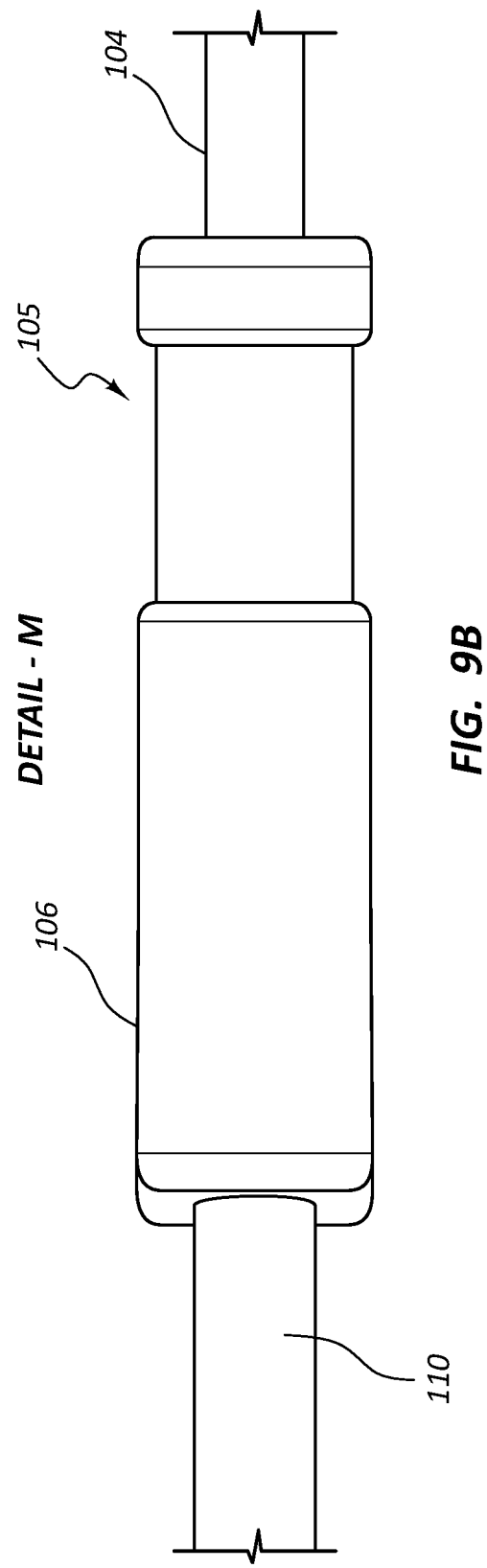

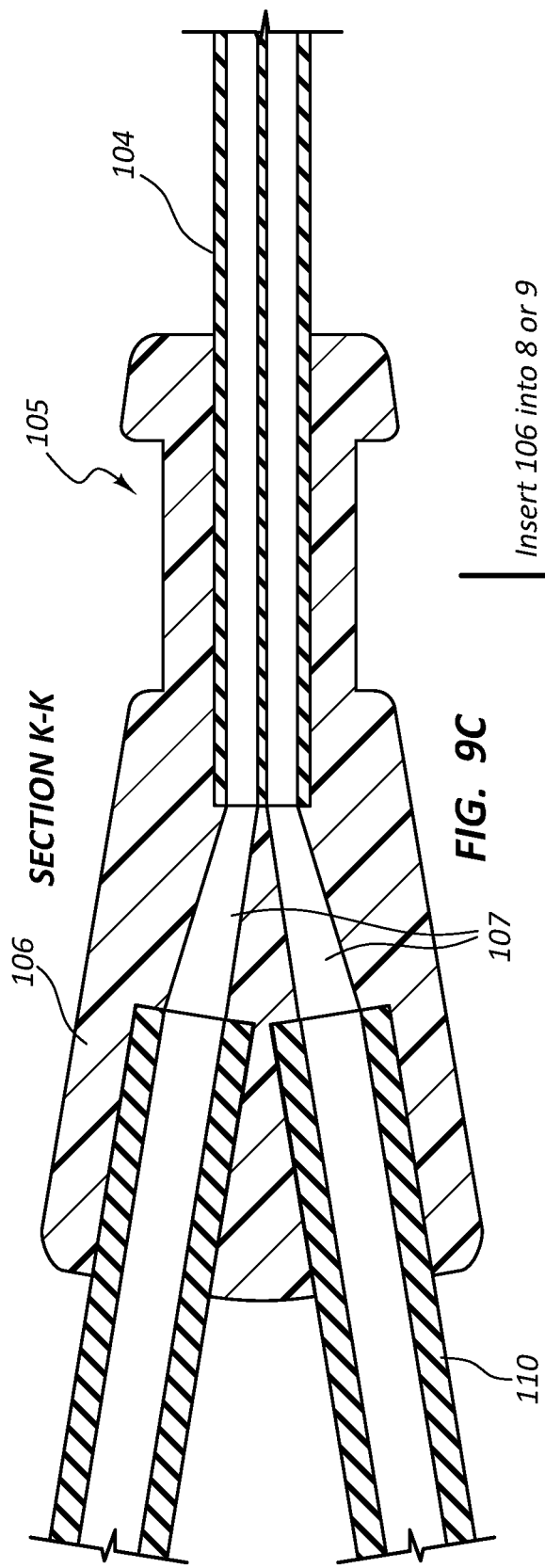
FIG. 9C
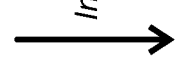
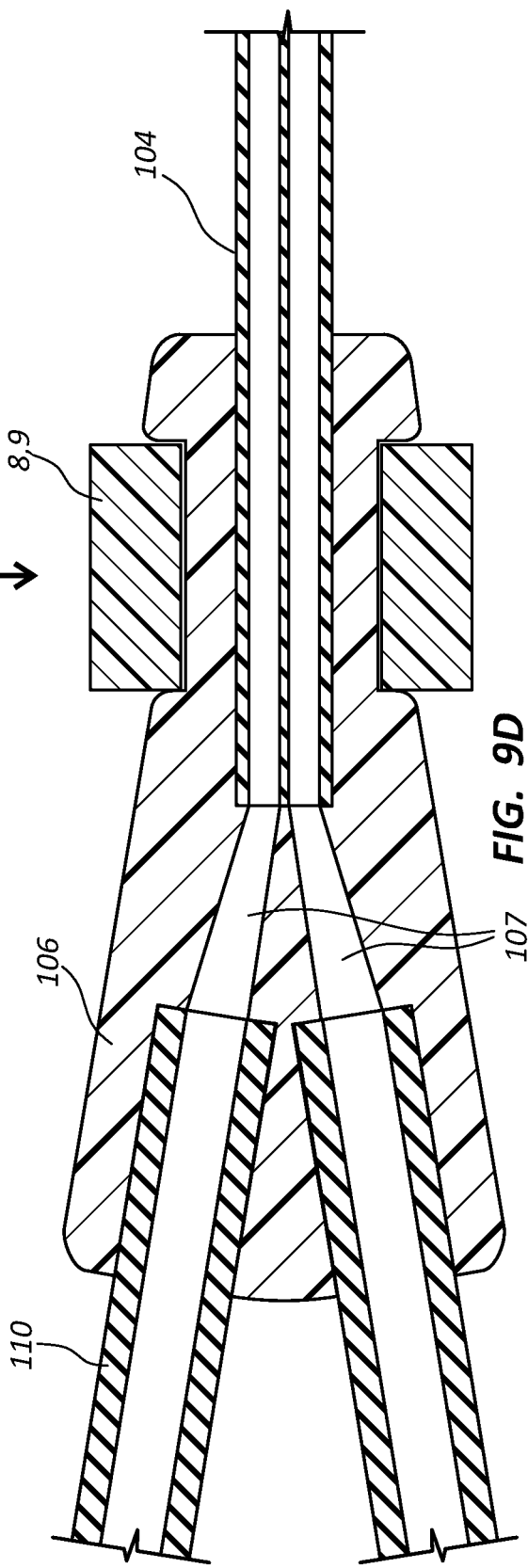
FIG. 9D

PERIPHERALLY INSERTED CENTRAL CATHETER SYSTEMS, DEVICES, AND METHODS THEREOF FOR PEDIATRICS

CROSS-REFERENCE

This application claims the benefit of U.S. Provisional Patent Application No. 62/336,557, filed May 13, 2016, which is hereby incorporated by reference herein in its entirety.

BACKGROUND

Peripherally inserted central catheters ("PICCs") are commonly used in medicine for long-term vascular access for administration of medication, nutrition, or both medication and nutrition to patients. PICCs are likewise used in neonates and infants for the administration of medication and nutrition when such neonatal or infant patients are unable to effectively nurse or where their gastrointestinal tracts might not be sufficiently developed for digestion. Such PICCs are designed with smaller profiles for the smaller neonatal and infant patients; however, the smaller profiles and smaller features thereof are not without complications such as accidental dislodgment and breakage. Provided herein are systems and methods that address the foregoing.

SUMMARY

Provided herein is a PICC for pediatric patients including, in some embodiments, a catheter tube, one or more extension legs, and a junction coupling a proximal end of the catheter tube to the one or more extension legs. The catheter tube can include a tapered portion that extends from a proximal end of the catheter tube to a medial portion of the catheter tube. The tapered portion of the catheter tube can include a first outer diameter with a first wall thickness at the proximal end of the catheter tube and a second, smaller outer diameter with a second, thinner wall thickness at the medial portion of the catheter tube. The junction can include a circumferentially recessed portion about an outer diameter of the junction configured to interlock with a securement device to inhibit movement of the junction when the PICC is inserted in a pediatric patient such as a neonatal patient.

Also provided herein is a catheterization system for treatment of pediatric patients including, in some embodiments, a PICC and a securement device. The PICC can include a catheter tube joined to one or more extension legs with a junction. The catheter tube can include a taper proximate the junction. The taper can transition the catheter tube in a proximal to distal direction from a first outer diameter and a first wall thickness to a second outer diameter smaller than the first outer diameter and a second wall thickness smaller than the first wall thickness. The securement device can be configured to fit around a recessed portion of an outer diameter of the junction to inhibit movement of the junction when the junction is held in the securement device.

Also provided herein is a method for treatment of pediatric patients including, in some embodiments, obtaining a catheterization system, navigating a catheter of the catheterization system to a desired location in a patient's body, and securing the catheter in a securement device of the catheterization system. The catheterization system can include the foregoing catheter with the tapered catheter tube joined to the one or more extension legs with the junction. The catheterization system can further include the foregoing securement device configured to fit around the recessed portion of the outer diameter of the junction. Navigating the catheter of the catheterization system to the desired location in the patient's body can include accessing an opening in the patient's skin before navigating the catheter to the desired location in the patient's body. Securing the catheter in the securement device of the catheterization system can include attaching the securement device to the patient's skin and attaching the junction of the catheter to the securement device, thereby inhibiting movement of the junction when the junction is held in the securement device.

DRAWINGS

The disclosed devices, components, assemblies, systems and methods can be better understood with reference to the description taken in conjunction with the following drawings, in which like reference numerals identify like elements. The components in the drawings are not necessarily to scale.

FIG. 3A shows a detailed side view of a catheter tube of the catheter of FIG. 1A in accordance with some embodiments.

FIG. 3B shows a cross-sectional view of the catheter tube of FIG. 1A in a proximal-end portion of the catheter tube in accordance with some embodiments.

FIG. 3C shows a cross-sectional view of the catheter tube of FIG. 1A in a medial portion of the catheter tube in accordance with some embodiments.

FIG. 4C shows a cross-sectional view of the junction of the catheter of FIG. 1A in accordance with some embodiments.

FIG. 4D shows a cross-sectional view of the junction of the catheter of FIG. 1A in a securing device in accordance with some embodiments.

FIG. 5A shows a detailed side view of a luer connector of the catheter of FIG. 1A or FIG. 6A in accordance with some embodiments.

FIG. 5B shows a first cross-sectional view of the luer connector of the catheter of FIG. 1A or FIG. 6A in accordance with some embodiments.

FIG. 5C shows a second cross-sectional view of the luer connector of the catheter of FIG. 1A or FIG. 6A in accordance with some embodiments.

FIG. 8A shows a detailed top view of a catheter tube of the catheter of FIG. 6A in accordance with some embodiments.

FIG. 8B shows a cross-sectional view of the catheter tube of FIG. 6A in a proximal-end portion of the catheter tube in accordance with some embodiments.

FIG. 8C shows a cross-sectional view of the catheter tube of FIG. 6A in a medial portion of the catheter tube in accordance with some embodiments.

FIG. 9A shows a detailed top view of a junction of the catheter of FIG. 6A in accordance with some embodiments.

FIG. 9B shows a detailed side view of a junction of the catheter of FIG. 6A in accordance with some embodiments.

FIG. 9C shows a cross-sectional view of the junction of the catheter of FIG. 6A in accordance with some embodiments.

FIG. 9D shows a cross-sectional view of the junction of the catheter of FIG. 6A in a securing device in accordance with some embodiments.

Figure 1A:
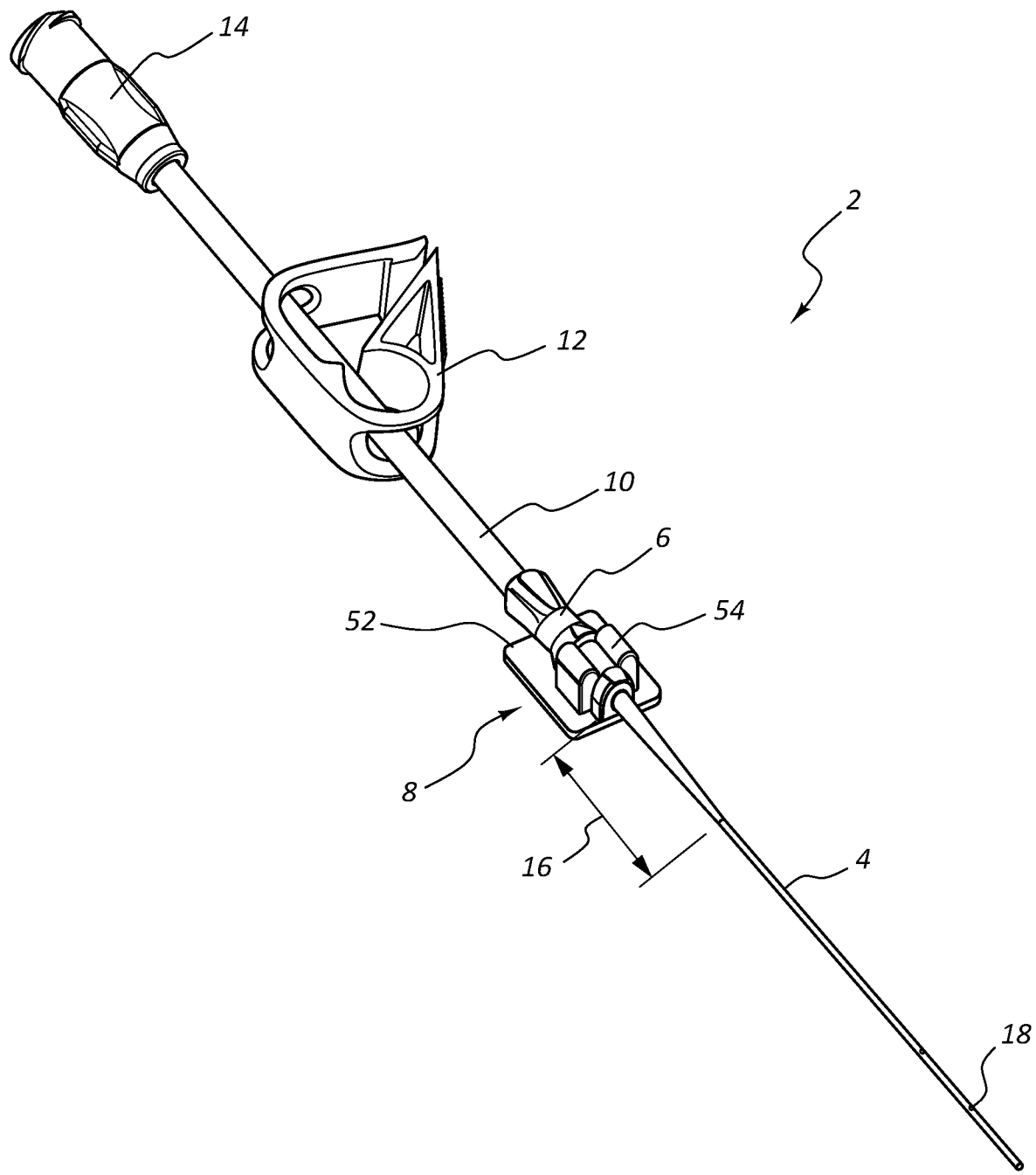
FIG. 1A shows a perspective view of a catheter configured as a single-lumen PICC with a first securement device attached thereto in accordance with some embodiments.

While the invention is susceptible to various modifications and alternative forms, specific embodiments thereof are shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION

Described herein are devices, components, assemblies, systems, methods, etc. for catheters and securement devices. The description and accompanying figures, which describe and show certain embodiments, are made to demonstrate, in a non-limiting manner, several possible configurations of catheters, securement devices, apparatuses, devices, components, assemblies, systems, etc. and various methods of using them according to various aspects and features of the present disclosure. Accordingly, the disclosure is not limited to the specific embodiments described. Rather, the inventive principles associated with the embodiments described herein, including with respect to the apparatuses, devices, components, assemblies, systems, methods, etc. described herein, can be applied in a variety of ways, including to other types of apparatuses, devices, components, assemblies, systems, methods, etc. General and specific apparatuses, devices, components, assemblies, systems, methods, etc. are described herein sufficiently to enable one to develop a variety of implementations/applications without undue experimentation. In the development of particular applications, numerous implementation-specific decisions can be made to achieve the design-specific goals, which can vary from one implementation/application to another. It will be appreciated that, having access to this disclosure and reading this disclosure, such a development effort can be a routine undertaking for other persons of ordinary skill in the art.

This document does not intend to distinguish between components that differ in name but not function. In the following discussion and in the claims, the terms "including," "includes," "comprising," "comprises," "having," "has," and "with" are used in an open-ended fashion, and thus should be interpreted to mean "including, but not limited to."

PICCs are commonly used in medicine for long-term vascular access for administration (e.g., infusion) of medication, nutrition, or both medication and nutrition to patients. PICCs are likewise used in neonates and infants for the administration of medication and nutrition when such neonatal or infant patients are unable to effectively nurse or where their gastrointestinal tracts might not be sufficiently developed for digestion. Such PICCs are designed with smaller profiles for the smaller neonatal and infant patients; however, the smaller profiles and smaller features thereof are not without complications such as accidental dislodgment and breakage. Provided herein are systems and methods that address the foregoing.

A catheterization system for treatment of patients (e.g., pediatric or neonatal patients) is provided in some embodiments. The catheterization system can include a catheter (e.g., a PICC) and a securement device. The catheter can be a single lumen, dual-lumen, triple-lumen, or multi-lumen catheter. The catheter can comprise a catheter tube joined to an extension leg with a junction/bifurcation. The catheter tube can include a taper proximate the junction/bifurcation. The taper can transition the catheter tube from a first outer diameter and first wall thickness to a second outer diameter smaller than the first outer diameter and a second wall thickness smaller than the first wall thickness in a proximal to distal direction. The taper can be configured to prevent the catheter tube from breaking in the region proximate the junction. The first wall thickness can be at least twice, three times, or four times as thick as the second wall thickness.

The catheterization system can include a single-lumen catheter, a dual-lumen catheter, one or more securement devices, or any combination of these. The single-lumen catheter and/or the dual-lumen catheter can be constructed or designed as a PICC, and can be manufactured or formed of one or more of a variety of materials, e.g., polymer materials, polyurethane (e.g., one or more thermoplastic urethanes), silicone, latex, HDPE, PTFE, etc. The single-lumen catheter and/or the dual-lumen catheter can be of various sizes, e.g., 1 Fr, 2 Fr, 3 Fr, 4 Fr, 5 Fr, 6 Fr, 7 Fr, 8 Fr, 9 Fr, etc. In one embodiment, one or both of the single-lumen catheter and the dual lumen catheter can be 2 Fr polyurethane PICCs. The catheters or PICCs can have short thick tapers or tapered regions. The short thick taper can resist breakage at the hub and ease manufacturing. The short thick taper can be configured or designed to fit on or for use on a pediatric patient including a neonatal patient. The single-lumen catheter and/or the dual-lumen catheter can include luers or luer connectors on an end thereof (e.g., a proximal end). The luers or luer connectors can have one or more reduced dimensions (e.g., a reduced length) compared to other catheters or PICCs for adolescents and adults; that is, the luers or luer connectors can be sized for a pediatric or neonatal patient.

For example, the foregoing catheterization system can include a single-lumen PICC, a dual-lumen PICC, one or more securement devices, or any combination of these. The single lumen PICC and/or dual lumen PICC can be manufactured or formed of a variety of materials. The single lumen PICC and/or dual lumen PICC can be of various sizes, e.g., 2 Fr, 3 Fr, 4 Fr, etc. In one embodiment, one or both of the single lumen PICC and the dual lumen PICC can be 2 Fr polyurethane PICCs. The PICCs can have short thick tapers or tapered regions. The short thick taper can resist breakage at the hub and ease manufacturing (e.g., handling the catheters or PICCs without breakage during manufacturing). The short thick taper can be configured or designed to fit on or for use on a pediatric patient including a neonatal patient. The single lumen PICC and/or dual lumen PICC can include luers or luer connectors on an end thereof (e.g., a proximal end). The luers or luer connectors can have one or more reduced dimensions (e.g., a reduced length) compared to other PICCs.

The single-lumen catheter and/or the dual-lumen catheter can include a junction. The junction can be configured or designed to fit on pediatric anatomy including neonate anatomy. The junction can be configured or designed to fit into a securement device (e.g., similar to a Statlock® securement device). The single-lumen catheter and/or the dual-lumen catheter can also include or be used with wings (e.g., suture wings) that can be removable (e.g., to provide the smallest possible configuration). The wings can be used for a configuration slightly or somewhat larger than the smallest configuration (e.g., a next smallest configuration). The wings can be left on the catheter or junction of the catheter and can themselves or a portion thereof can fit into a securement device (e.g., a barbed or posted [with posts] Statlock® device), wherein the securement device can have a reduced wing span.

For example, the foregoing single lumen catheter and/or dual lumen catheter can include a single lumen PICC and/or dual lumen PICC with a junction. The junction can be configured or designed to fit on pediatric anatomy including neonate anatomy. The single lumen PICC and/or dual lumen PICC can include wings that can be removable (e.g., to provide the smallest possible configuration). The junction can be configured or designed to fit into a securement device (e.g., the same as or similar to a Statlock securement device or a redesigned universal Statlock device). This can be used for a configuration slightly or somewhat larger than the smallest configuration (e.g., a next smallest configuration). The wings can be left on and fit into a securement device (e.g., a barbed or posted [with posts] Statlock, or a similar securement device with a reduced wing span).

In one embodiment, the catheters and securement devices are configured and designed for use with pediatric or neonatal patients. The components of the catheters and securement devices can have smaller dimensions and other changes to create or use a smaller footprint or area when used on a small patient. While such catheters or PICCs are relatively small, the securement devices are configured to minimize catheter micromotion as well as accidental removal or dislodgement.

Figure 1B:
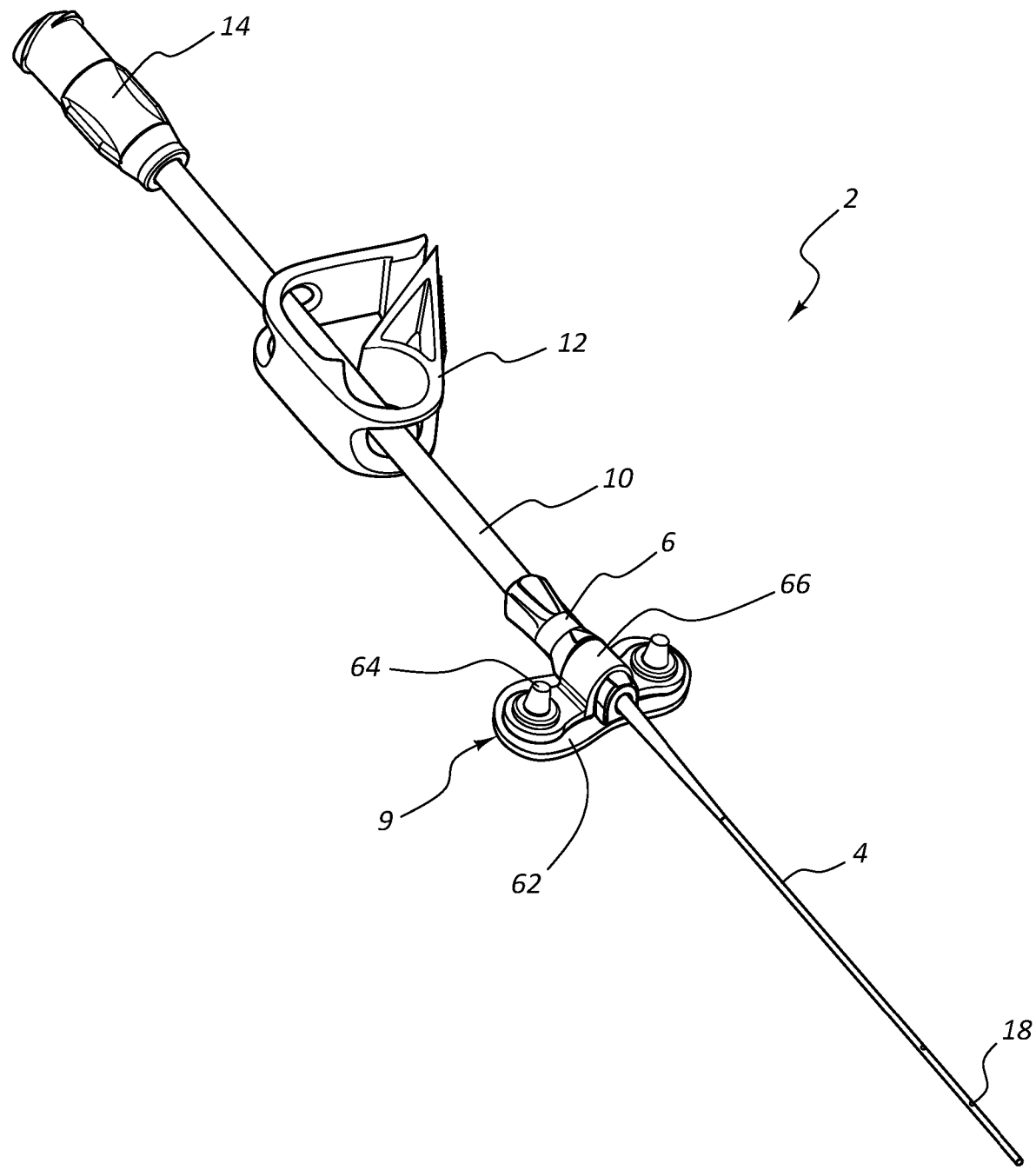
FIG. 1B shows a perspective view of the catheter of FIG. 1A with a second, different securement device attached thereto in accordance with some embodiments.
Figure 2A:
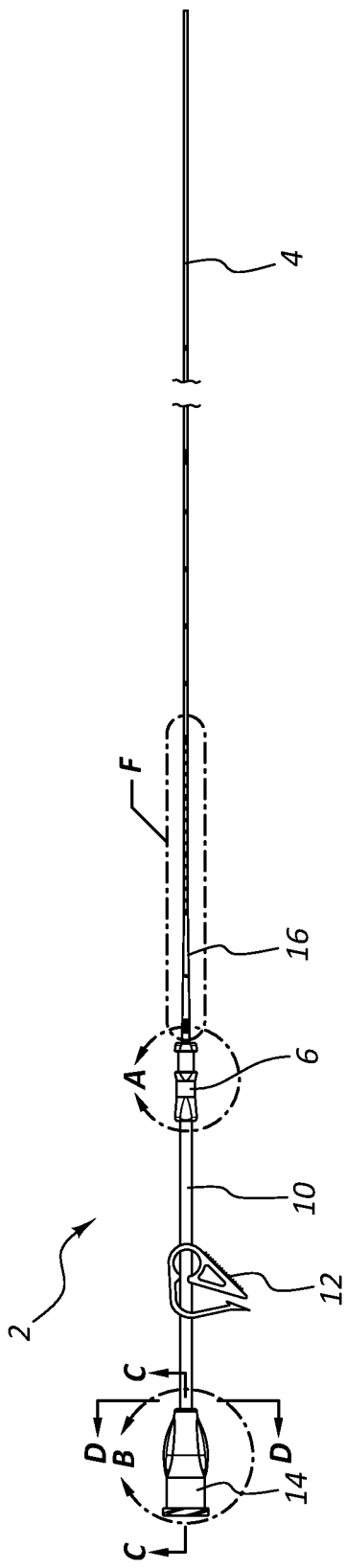
FIG. 2A shows a side view of the catheter of FIG. 1A in accordance with some embodiments.
Figure 2B:
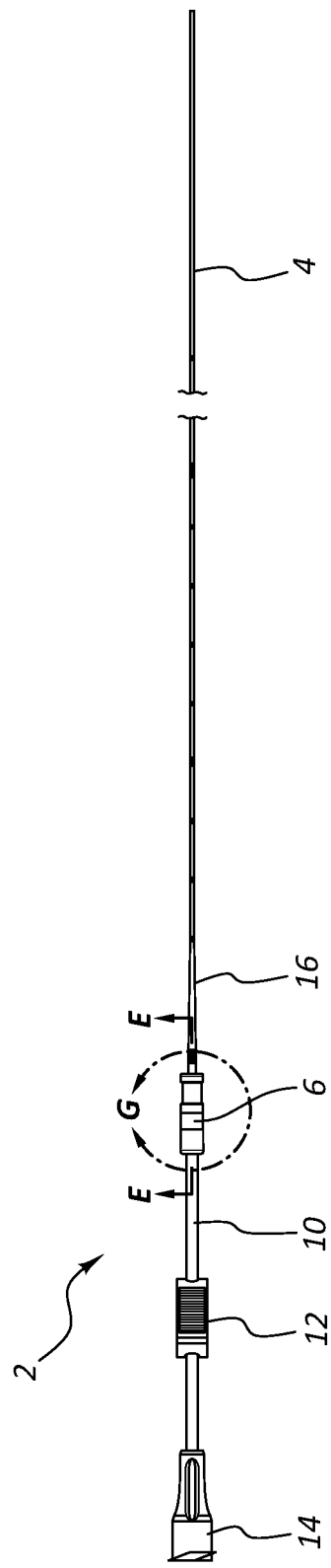
FIG. 2B shows a top view of the catheter of FIG. 1A in accordance with some embodiments.
Figure 6A:
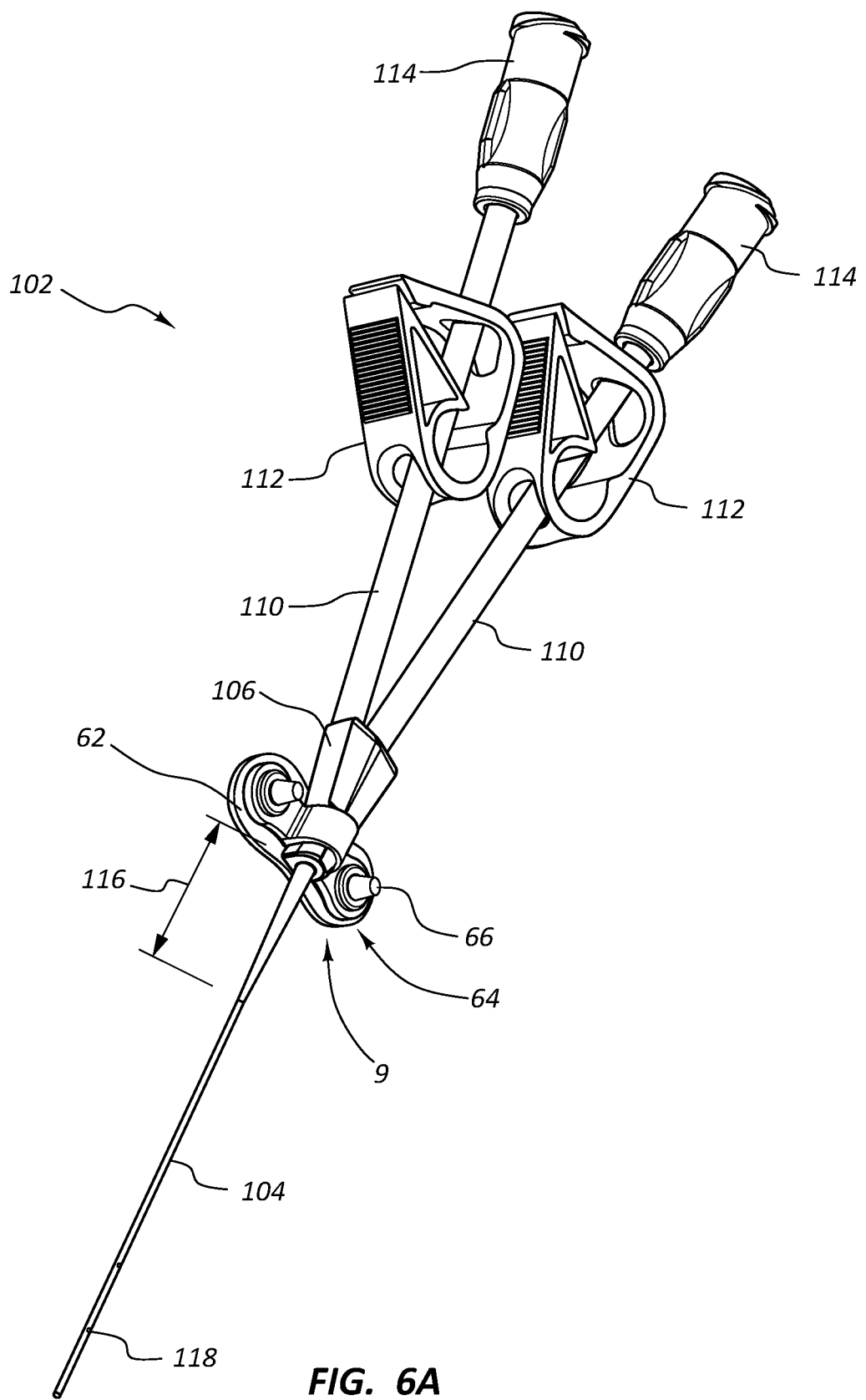
FIG. 6A shows a perspective view of a catheter configured as a dual-lumen PICC with a first securement device attached thereto in accordance with some embodiments.
Figure 6B:
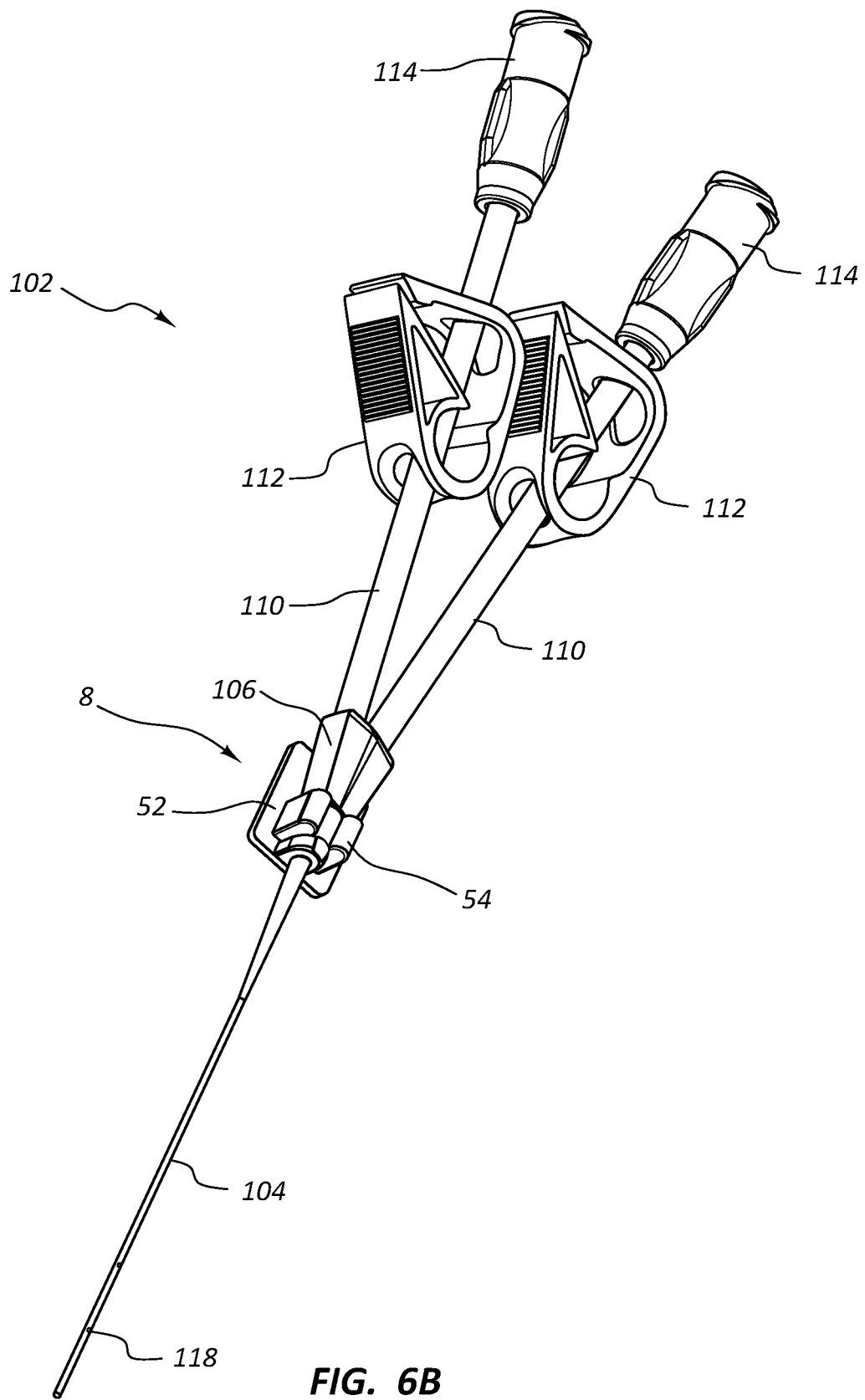
FIG. 6B shows a perspective view of the catheter of FIG. 6A with a second, different securement device attached thereto in accordance with some embodiments.
Figure 7A:
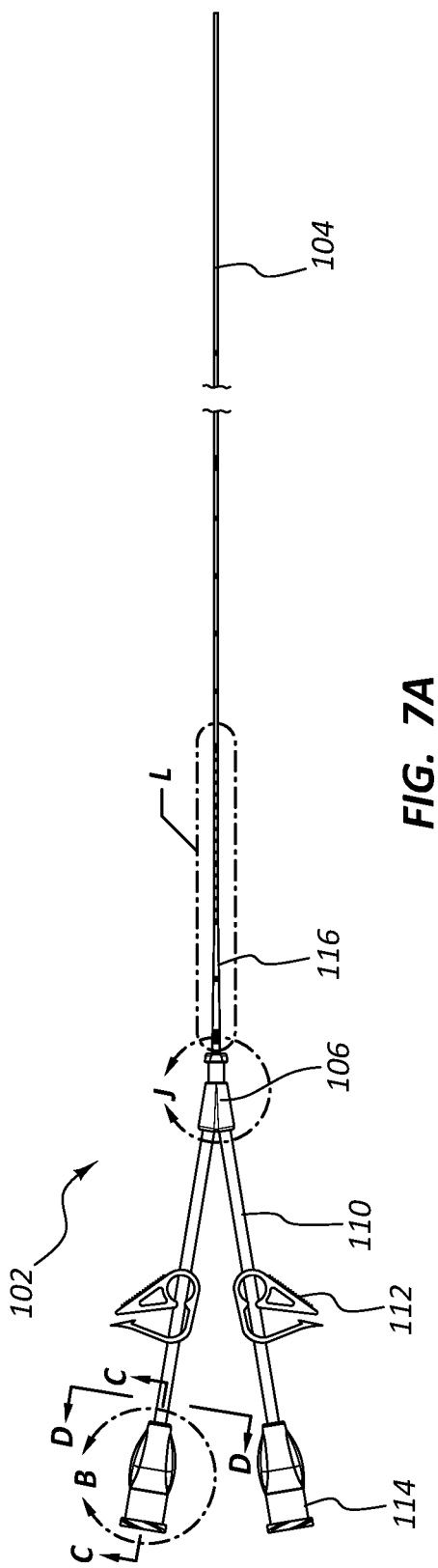
FIG. 7A shows a top view of the catheter of FIG. 6A in accordance with some embodiments.
Figure 7B:
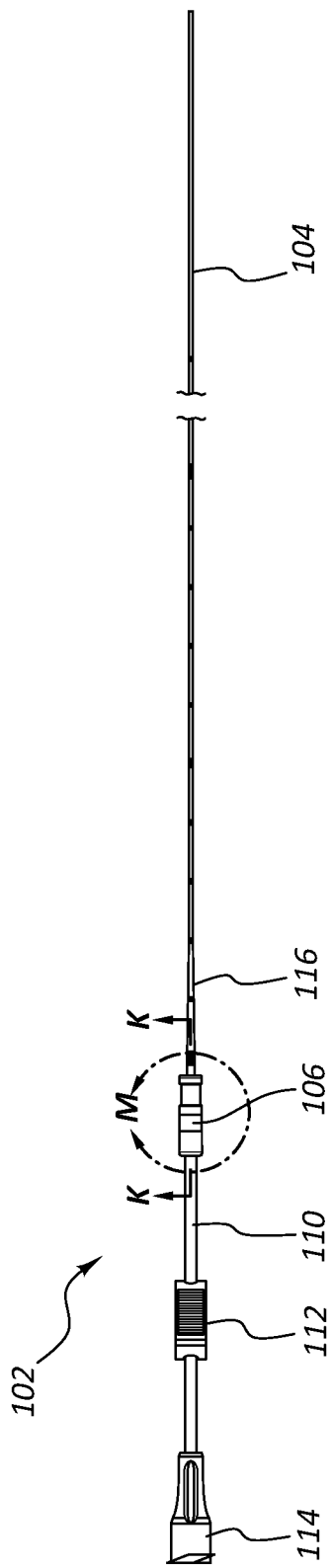
FIG. 7B shows a side view of the catheter of FIG. 6A in accordance with some embodiments.

FIGS. 1A and 1B show perspective views of a proximal region of a single-lumen catheter 2 in different securement devices, FIG. 2A shows a side view of the entire catheter 2, and FIG. 2B shows a top view of the entire catheter 2. The catheter 2 of the foregoing figures is configured as a PICC with a short thick taper and a junction that can be connected to a securement device or multiple securement devices. FIGS. 6A and 6B show perspective views of a proximal region of a dual-lumen catheter 102 in different securement devices, FIG. 7A shows a side view of the entire catheter 102, and FIG. 7B shows a top view of the entire catheter 102. The catheter 102 of the foregoing figures is also configured as a PICC with a short thick taper and a junction that can be connected to a securement device or multiple securement devices. The distal end of catheter/PICCs 2 and 102 can extend further (e.g., be longer) than shown in FIGS. 1A, 1B, 6A, and 6B. (See FIGS. 2A, 2B, 7A, and 7B.) The PICCs 2 and 102 can include a catheter tube 4 or 104, a bifurcation/junction 6 or 106, a securement device 8, 9, 108, or 109, an extension leg 10 or 100, a clamp 12 or 112, a luer or luer connector 14 or 114, other components, or a combination of some or all of these.

The catheter tube 4 or 104 can be formed of any one or more of a variety of materials (e.g., polyurethane, latex, silicone, another polymer or plastic material, other materials mentioned herein, etc.), and the catheter tube can be formed in a variety of ways (e.g., extrusion, bump extrusion, molding such as injection molding, etc.). For example, the catheter tube 4 or 104 can be formed of a thermosetting polyurethane or a thermoplastic polyurethane including a block copolymer of polyurethane such as an aromatic polycarbonate-based thermoplastic polyurethane (e.g., Quadrathane™ ARC), an aliphatic thermoplastic polyurethane (e.g., Quadraflex™ ALE), or an aliphatic polyether-based thermoplastic polyurethane (e.g., Tecoflex™ 93A). Use of materials such as thermoplastic polyurethane enables embodiments of catheters or PICCs in which the catheter tube softens upon warming such as upon insertion in a pediatric or neonatal patient and warming to body temperature. In such embodiments, the catheters are configured to soften upon warming but not to such a degree that catheter-tube integrity is compromised.

The catheter tube 4 or 104 can be a variety of sizes, e.g., 1 Fr, 2 Fr, 3 Fr, 4 Fr, 5 Fr, 6 Fr, 7 Fr, 8 Fr, 9 Fr, etc. In one embodiment, a neonatal PICC 2 or 102 can have an extruded polyurethane catheter tube about 2 Fr at its distal end. The size of the catheter tube 4 or 104 can be different at different portions of the catheter tube 4 or 104, e.g., the catheter tube 4 or 104 can include one or more transitions or tapers 16 or 116 between sizes. In one embodiment, the taper 16 or 116 can be a short thick taper. As used herein, "short taper" includes a taper or tapered portion of an elongate member such the catheter tube 4 or 104 that occurs over a relatively small length of the elongate member. With respect to the catheter tube 4 or 104, the relatively small length of the short taper can include up to about 25% of a total length of the catheter tube, including up to about 20% of the total length of the catheter tube, such as up to about 15% of the total length of the catheter tube, for example, up to about 10% or 5% of the total length of the catheter tube. Of the foregoing, the relatively small length of the short taper can include more than 1% of the total length of the catheter tube, including more than about 2% of the total length of the catheter tube, such as more than about 3% of the total length of the catheter tube, for example, more than about 4% or 5% of the total length of the catheter tube. For example, the tapered portion of the catheter tube can be more than about 5% and up to about 10% (e.g., between 5% and 10%) of the total length of the catheter tube, such as about 9% of the total length of the catheter tube. This can be 0.5-3 inches, 1-2 inches, or about 2 inches (±0.1 inches) for the relatively small length of the short taper in some embodiments. As used herein, "thick taper" includes a taper or tapered portion of an elongate member such as the catheter tube 4 or 104 that has relatively thick walls compared to walls of the elongate member outside the taper or tapered portion. With respect to the catheter tube 4 or 104, the relatively thick walls can include a wall thickness about 2-5 times thicker, including about 2-4 times thicker, such as about 2-3 times thicker, for example, about 2 or 3 times thicker in the taper or tapered portion of the catheter tube than the wall thickness at the distal end or a medial portion of the catheter tube 4 or 104. In one embodiment, the taper 16 or 116 can transition from a 4 Fr size to a 2 Fr size or other combinations or transitions involving the various French sizes disclosed above. In view of the foregoing, a "short thick taper," includes characteristics of both a "short taper" and a "thick taper."

The taper 16 or 116 can occur at a proximal end of the catheter tube 4 or 104 proximate the junction 6 or 106 as shown in FIGS. 1A and 3A for the catheter tube 4 and FIGS. 6A and 8A for catheter tube 104, or the taper 16 or 116 can be at another location along the catheter tube 4 or 104. A tapered catheter tube 4 or 104 having thicker walls at a proximal end of the catheter helps to protect the catheter against damage or breaking near the junction 6 or 106. The proximal end of the catheter tube can have a wall thickness sufficiently thick to prevent or otherwise protect the catheter against breakage about the proximal end of the catheter tube when the catheter is handled or inserted in a pediatric or neonatal patient, particularly when done in accordance with instructions for use of the catheter. (A catheterization system provided herein can include such instructions for use.) The thicker walls allow the catheter to flex or bend near the junction 6 or 106 (e.g., when the catheter is placed on and secured to a small or neonatal patient's body) without a high risk of rupture or other damage. This is especially important in smaller PICC sizes for pediatric or neonatal patients that can otherwise be at more risk because of their small size.

FIGS. 3A, 3B, and 3C show the tapered catheter tube 4 of the single-lumen catheter 2 having thicker walls in the proximal-end section of the catheter tube 4 than in the distal-end section of the catheter tube 4. In addition, the size or diameter d of the single lumen of the catheter tube 4 can remain the same or about the same as the wall thickness decreases over the taper 16 through to the distal-end section where the wall thickness is constant or about constant. FIGS. 8A, 8B, and 8C also show the tapered catheter tube 104 of the dual-lumen catheter 102 having thicker walls in the proximal-end section of the catheter tube 104 than in the distal-end section of the catheter tube 104. In addition, the size or height h1 and width w1 of each lumen of the dual-lumen catheter tube 104 can lessen as the wall thickness decreases over the taper 116 through to the distal-end section where the wall thickness and the size or height h2 and width 1422 of each lumen are constant or about constant. That being said, in some embodiments, w1 and 1422 can be constant or about constant over the entire length of the catheter tube 104, and h1 and h2 can be constant or about constant over the length of the catheter tube 104.

The catheter tube 4 or 104 can include one or more tapers, each of which can go from a larger diameter to smaller diameter or from a smaller diameter to a larger diameter in any direction from proximal to distal or distal to proximal. In one embodiment, the distal end includes a taper or flare transitioning from a smaller diameter to a larger diameter at the distal end or distal tip. The changing outer diameter of the taper can be accomplished with a change in wall thickness over the taper, a change in size/diameter of the lumen(s) over the taper, or both. In one embodiment, the size of the lumen(s) can remain the same or about the same over the taper while the wall thickness increases or decreases.

As shown in FIGS. 3A and 8A, and as shown in more detail in FIGS. 13A-13F, the catheter 2 or 102 (e.g., PICC 2 or 102) can include markers or markings 18 or 118 (e.g., depth or insertion markings) that can help a medical practitioner position the catheter (or tip thereof) as well as monitor migration of the catheter. With respect to positioning a catheter such as the catheter 2 or 102, a medical practitioner often initially inserts the catheter slightly deeper than needed in anticipation of a subsequent pull-back adjustment in accordance with a chest X-ray ("CXR"). Catheters are often positioned in this way to avoid replacing the catheter since the catheter should not or cannot be advanced more after initially inserting the catheter. In most cases, the catheter is pulled back 2-3 mm in a pull-back adjustment using an electronic caliper on the CXR to position the tip of the catheter just above the cardiac shadow in the $3^{rd}$ and $4^{th}$ posterior intercostal space. In some cases, a pull-back adjustment of 1-2 cm is needed; however, this is usually a result of an initial measuring mistake. In view of the foregoing, the catheter 2 or 102 includes the markings 18 or 118 in suitable increments over suitable ranges of the catheter configured to assist the medical practitioner in positioning the catheter as well as monitor migration of the catheter. The markings 18 or 118 can include different markings, different patterns of markings, or a combination thereof over different regions of the catheter tube 4 or 104 that assist the medical practitioner in positioning the catheter as well as monitor migration of the catheter.

One region of the different regions of the catheter tube 4 or 104 includes the taper 16 or 116. Markings 18 or 118 on the taper 16 or 116 can indicate where the taper begins and where the taper ends. For example, the taper 16 or 116 can include a zero marking (e.g., "0" or an indicator thereof such as the rectangle of FIGS. 3A and 8A) where the taper begins. The taper 16 or 116 can also include an end marking where the taper ends. Between the zero marking where the taper 16 or 116 begins and the end marking where the taper ends, any of a number of additional markings 18 or 118 (including no markings) can be used. As shown in FIGS. 3A, 8A, and 13A-13F, for example, the taper 16 or 116 is a total of about 3 cm in length, and markings 18 or 118 are used on the taper at every centimeter starting with the zero marking and ending with the end marking of the taper for a total of three 1-cm spaced markings.

Another region of the different regions of the catheter tube 4 or 104 includes a finely or more graduated region than the taper 16 or 116 that corresponds to a maximum recommended insertion depth for the catheter 2 or 102. Markings 18 or 118 on the finely graduated region can assist the medical practitioner in positioning the catheter including initially inserting the catheter and pulling back the catheter in a subsequent pull-back adjustment. Continuing in the proximal to distal direction set forth with respect to the taper 16 or 116, the finely graduated region can begin at the end marking of the taper, extend over a medial portion of the tube 4 or 104 proximate to the taper corresponding to at least a maximum anticipated pull-back adjustment (e.g., 3 cm), and end with an end marking of the finely graduated region. As shown in FIGS. 3A, 8A, and 13A-13F, for example, the finely graduated region is a total of about 3 cm in length to accommodate at least 1-2 cm pull-back adjustments corresponding to initial measurement errors, and the markings 18 or 118 are used in the finely graduated region at every centimeter starting with the end marking of the taper 16 or 116 and ending with the end marking of the finely graduated region. The markings 18 or 118 in the finely graduated region can further include markings at centimeter submultiples such as markings every 2 mm or every 2.5 mm. Such centimeter-submultiple markings 18 or 118 can assist the medical practitioner in pulling back the catheter in common pull-back adjustments of 2-3 mm. Such centimeter-submultiple markings 18 or 118 can also assist the medical practitioner in monitoring up to millimeter-based migrations of the catheter.

Figure 13A:
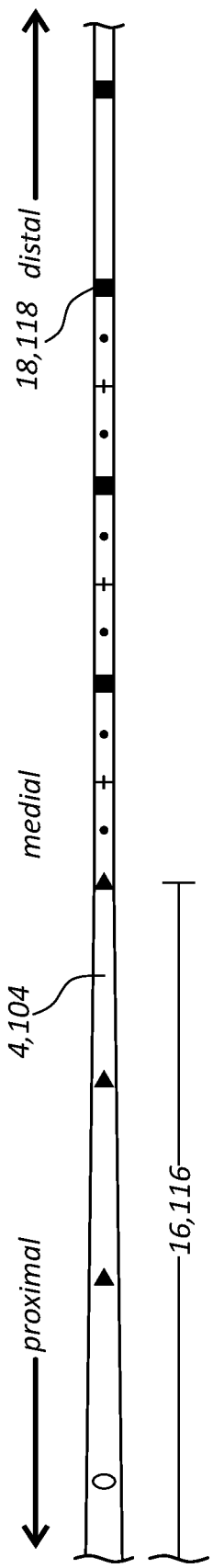
FIG. 13A shows a detailed view of a catheter tube with a first set of markings on the catheter tube in accordance with some embodiments.
Figure 13B:
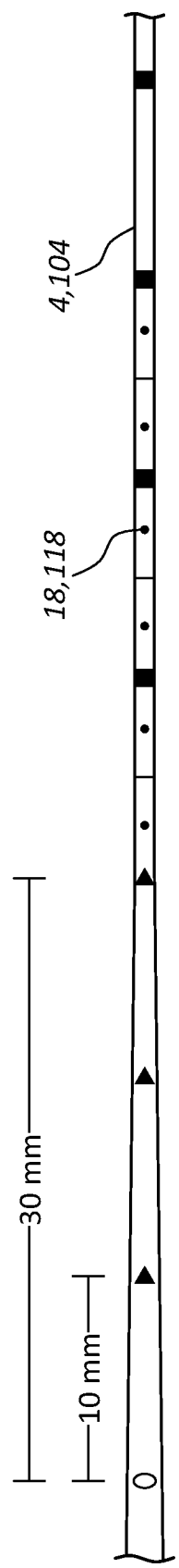
FIG. 13B shows a detailed view of a catheter tube with a second set of markings on the catheter tube in accordance with some embodiments.
Figure 13C:
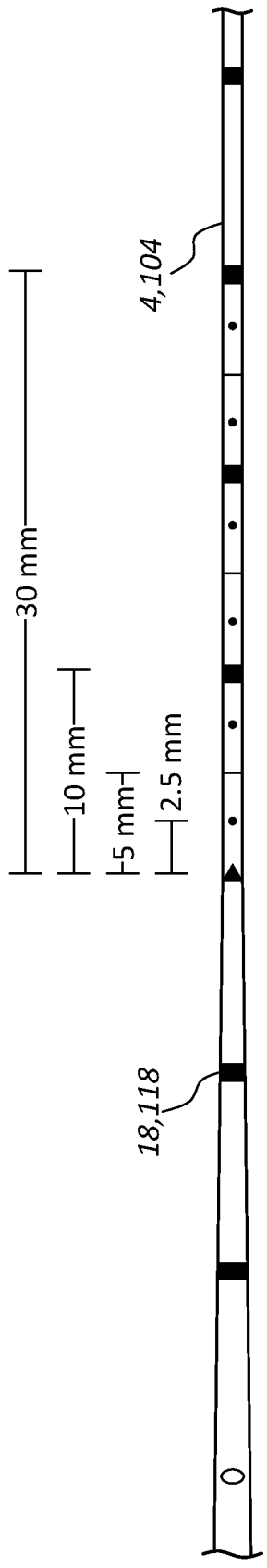
FIG. 13C shows a detailed view of a catheter tube with a third set of markings on the catheter tube in accordance with some embodiments.
Figure 13D:
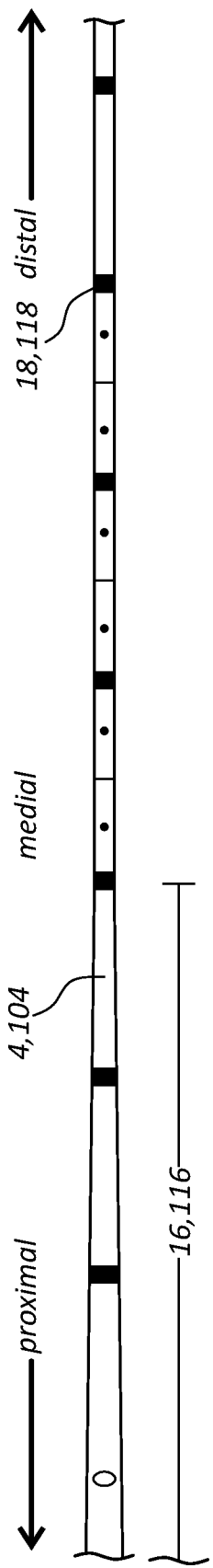
FIG. 13D shows a detailed view of a catheter tube with a fourth set of markings on the catheter tube in accordance with some embodiments.
Figure 13E:
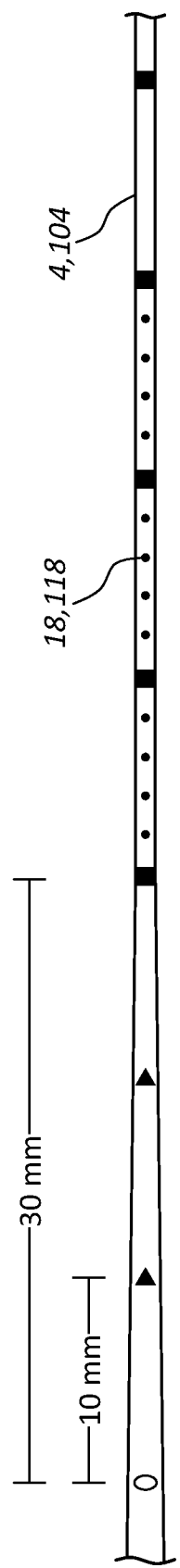
FIG. 13E shows a detailed view of a catheter tube with a fifth set of markings on the catheter tube in accordance with some embodiments.
Figure 13F:
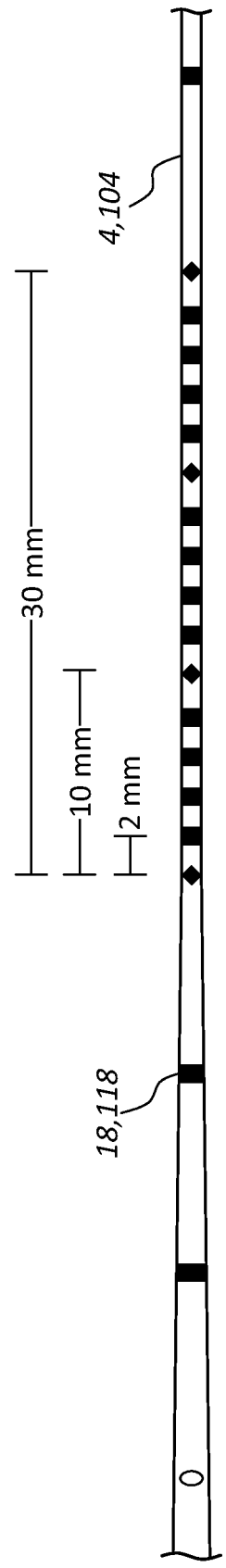
FIG. 13F shows a detailed view of a catheter tube with a sixth set of markings on the catheter tube in accordance with some embodiments.

As shown in FIGS. 3A, 8A, and 13A-13F the markings 18 or 118 can be lines (e.g., single lines, double lines, etc.), symbols (e.g., plus signs or crosses, minus signs or dashes, guillemets, etc.), open or filled shapes (e.g., squares, diamonds, rectangles, circles, triangles, etc.), other marks, or combination thereof that can indicate a measurement of length or distance. With respect to the foregoing combinations of the markings 18 or 118, different markings can indicate different multiples and submultiples of a unit of measurement such as filled squares every centimeter and filled circles every 2 mm or every 2.5 mm. For example, markings 18 and 118 as respectively shown in FIGS. 3A and 8A are a combination of filled squares, rectangles, and circles, whereas the markings shown in FIG. 13A are a combination of crosses and filled squares, triangles, and circles, and whereas the markings shown in FIG. 13F are a combination of filled squares and diamonds. Legibility at scale, medical practitioner preference, or a combination thereof can dictate which markings 18 or 118 of FIGS. 3A, 8A, and 13A-13F are used and how such markings are used. Again, such markings 18 or 118 can be, for example, 1 cm apart and optionally numerically marked (e.g., 0 cm, 5 cm, 10 cm, etc.) at regular intervals starting or ending at the proximal end of the tapered portion 16 or 116 of the catheter 2 or 102. And, again, such markings 18 or 118 can include centimeter-submultiple markings, especially in a region that can assist the medical practitioner in pulling back the catheter in common pull-back adjustments of 2-3 mm. The catheter tube 4 or 104 can be formed of a thermoplastic polyurethane. Use of materials such as thermoplastic polyurethane provides superior ink adhesion of the markings 18 or 118, for example, with respect to ink adhesion on silicone.

Figure 4A:
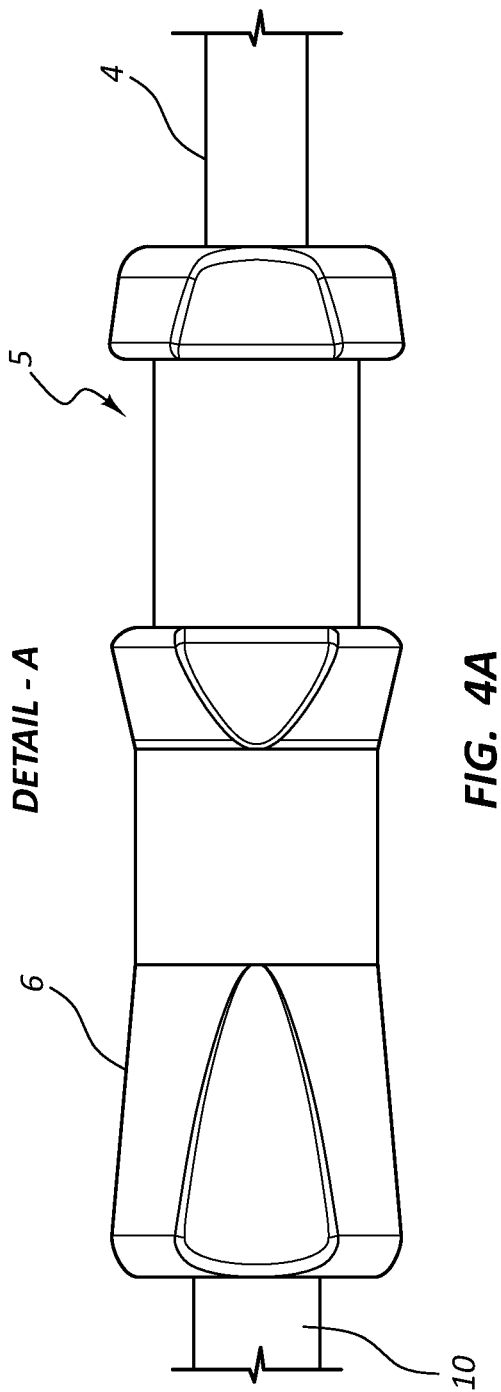
FIG. 4A shows a detailed side view of a junction of the catheter of FIG. 1A in accordance with some embodiments.
Figure 4B:
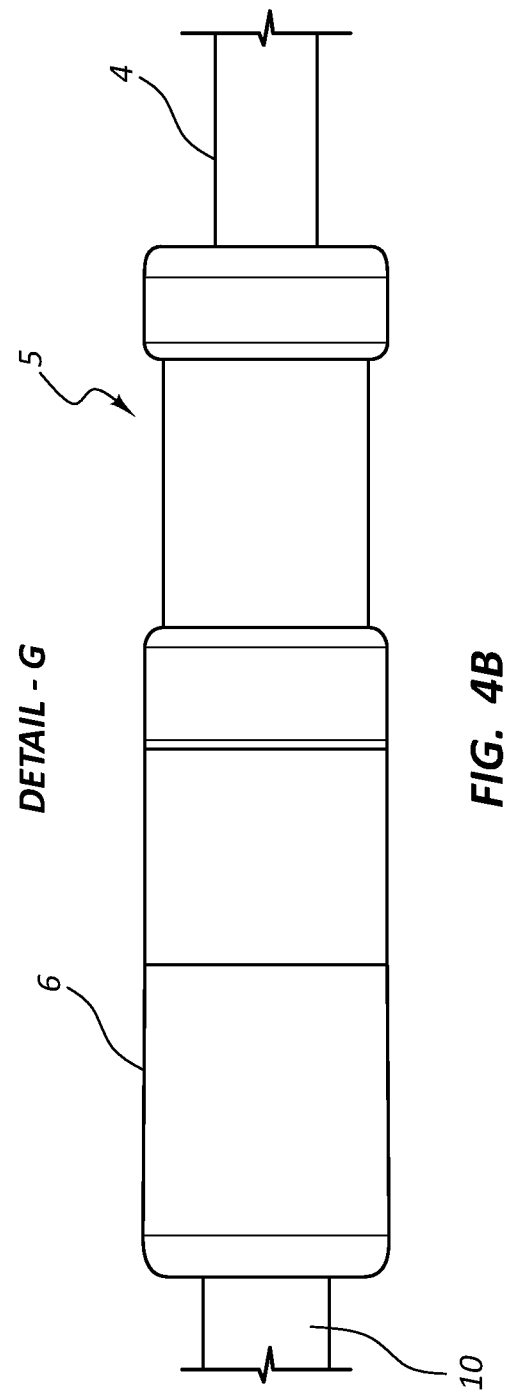
FIG. 4B shows a detailed top view of the junction of the catheter of FIG. 1A in accordance with some embodiments.

FIGS. 4A, 4B, and 4C respectively provide a side view, a top view, and a cross-sectional view of the junction 6 of the catheter 2. Likewise, FIGS. 9A, 9B, and 9C respectively provide a side view, a top view, and a cross-sectional view of the junction 106 of the catheter 102. Bifurcation/junction 6 or 106 can be formed of a variety of material in a variety of sizes and shapes. In one embodiment, the junction 6 or 106 is configured and designed to be as small as possible for comfort and use with very small patients, e.g., neonatal patients. As can be seen in FIGS. 4C and 9C, the proximal end of the catheter tube 4 or 104 can be captured, inserted, or enclosed in a distal end of the junction 6 or 106 or attached or coupled to the distal end of the junction 6 or 106. Likewise, the distal end of extension leg 10 or distal ends of extension legs 110 can be captured, inserted, or enclosed in a proximal end of the junction 6 or 106 or attached or coupled to the proximal end of the junction 6 or 106. As shown in each of FIGS. 4C and 9C, the junction 6 or 106 can include one or more tapered lumens therein configured to match lumen diameters of the one or more extension legs 10 or 110 and the catheter tube 4 or 104 in the junction 6 or 106. For example, the junction 6 can include a tapered lumen 7 therein configured to match the larger lumen diameter of the extension leg 10 to the smaller lumen diameter of the catheter tube 4. Likewise, the junction 106 can include a pair of tapered lumens 107 therein configured to match the larger lumen diameters of the pair of extension legs 10 to the smaller lumen diameters of the catheter tube 4. Flow rates through catheters with such junctions can be up to about 5.0 mL/min for single-lumen catheters and up to about 1.5 mL/min for each lumen in dual-lumen catheters.

The junction 6 or 106 can be formed in an overmolding process or another process. Overmolding can occur over the distal end of the extension leg 10 or over the distal ends of extension legs 110 and over the proximal end of the catheter tube 4 or 104. One or more pins, tubes, placeholders, or other connectors can be used between the distal end of the extension leg 10 or the distal ends of extension legs 110 and the proximal end of the catheter tube 4 or 104 to keep a lumen or lumens open between the tubes. Having a thicker wall of the proximal end of the catheter tube (i.e., in a catheter tube 4 or 104 with a proximal short thick taper) helps improve the overmolding process. The junction 6 or 106 can be formed of a harder or more rigid polymer or plastic material than the catheter tube 4 or 104. In one embodiment, the junction 6 or 106 can be formed of an aliphatic polyether-based thermoplastic polyurethane (e.g., Tecoflex™ 80A). The junction 6 or 106 can include a recessed region or slot on an outer surface configured and sized to be received and/or locked into a securement device.

The junction can be between 0.4 inches and 0.6 inches long and between 0.1 inches and 0.3 inches wide at its widest point. The junction can be between 0.45 inches and 0.55 inches long and between 0.1 inches and 0.2 inches wide at its widest point.

Various securement devices 8, 9, 108, and/or 109 can be used with the catheters disclosed herein (e.g., with catheter 2 and catheter 102). The securement devices 8, 9, 108, and/or 109 can be formed of a variety of materials (e.g., materials disclosed elsewhere herein or in the figures) and can be formed in a variety of shapes and sizes. A smaller size is desirable for smaller pediatric or neonatal patients. It can be difficult to find a size that works well functionally to secure and prevent undesired movement of the catheter while also having a small footprint or area of impact on the patient. As such, the securement devices 8, 9, 108, and/or 109 can be formed in a variety of shapes and smaller sizes desirable for smaller pediatric or neonatal patients.

Figure 11A:
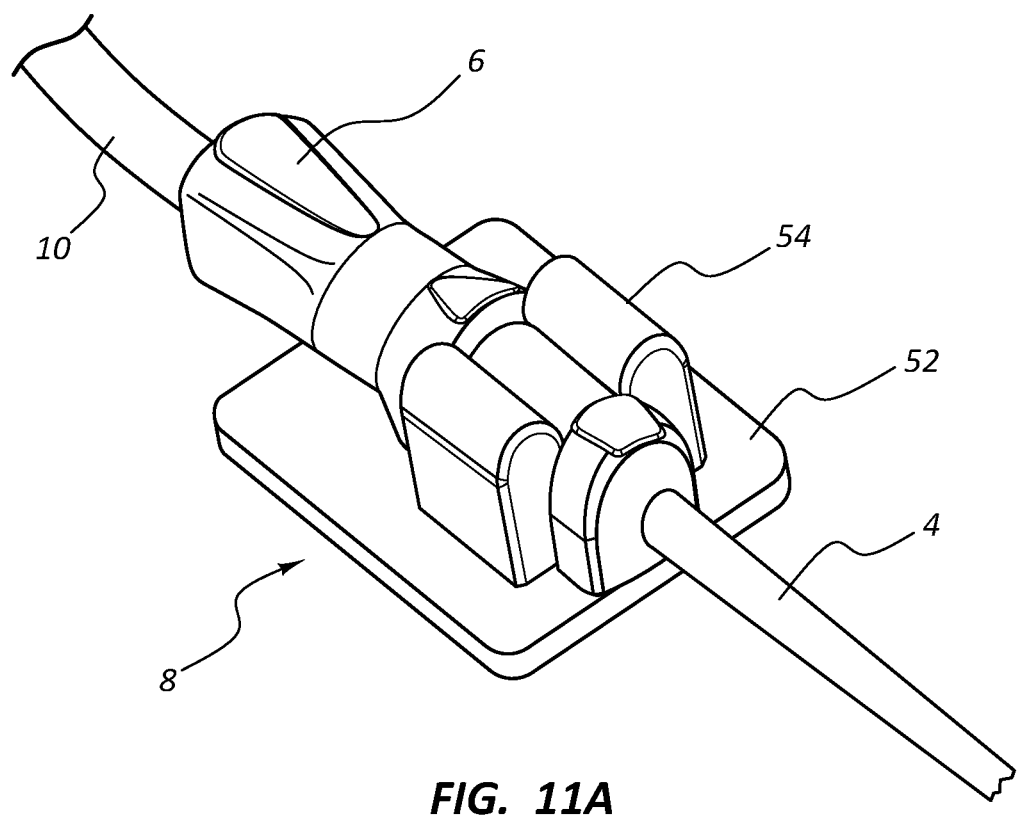
FIG. 11A shows a detailed view of the catheter of FIG. 1A secured in a first securement device in accordance with some embodiments.
Figure 11B:
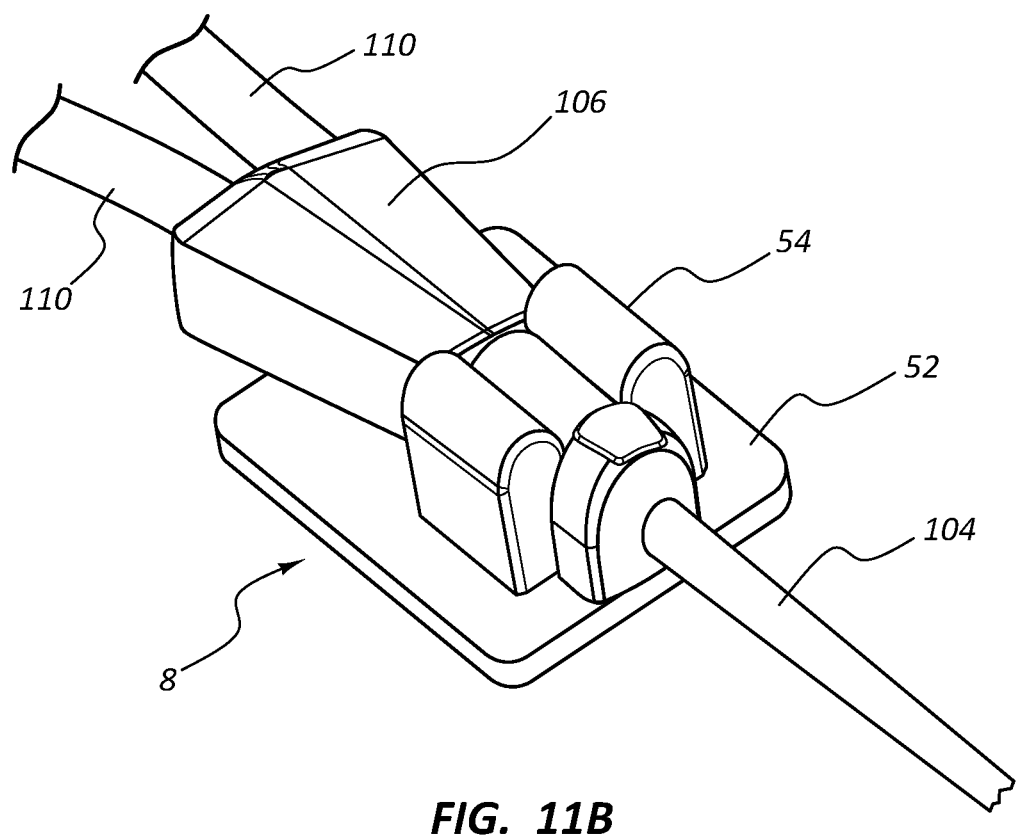
FIG. 11B shows a detailed view of the catheter of FIG. 6A secured in the first securement device in accordance with some embodiments.
Figure 11C:
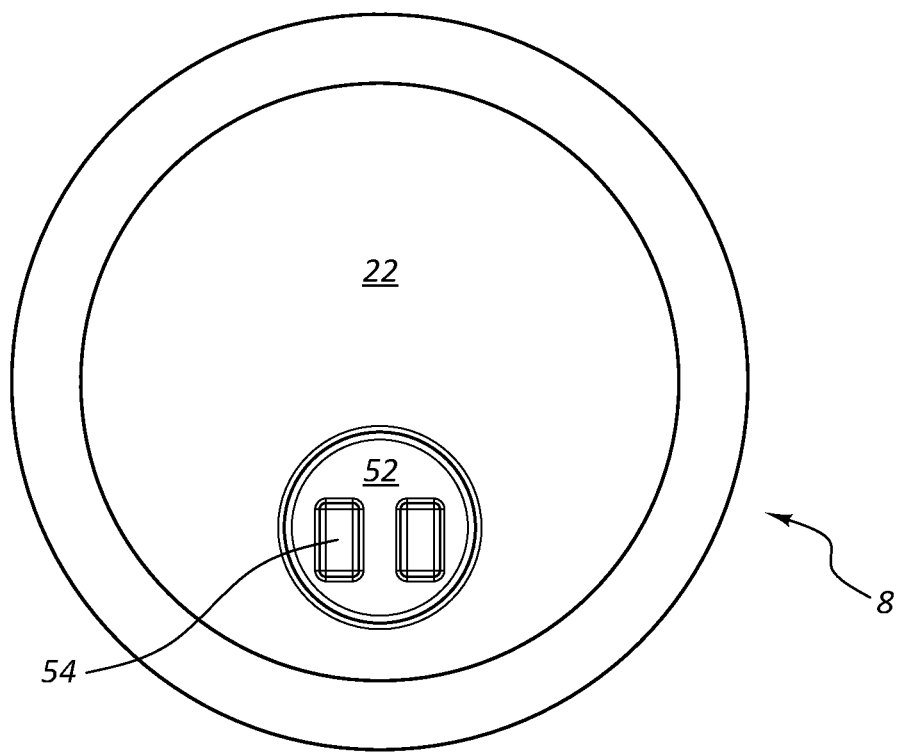
FIG. 11C shows a top view of the first securement device mounted on an adhesive pad in accordance with some embodiments.
Figure 11D:
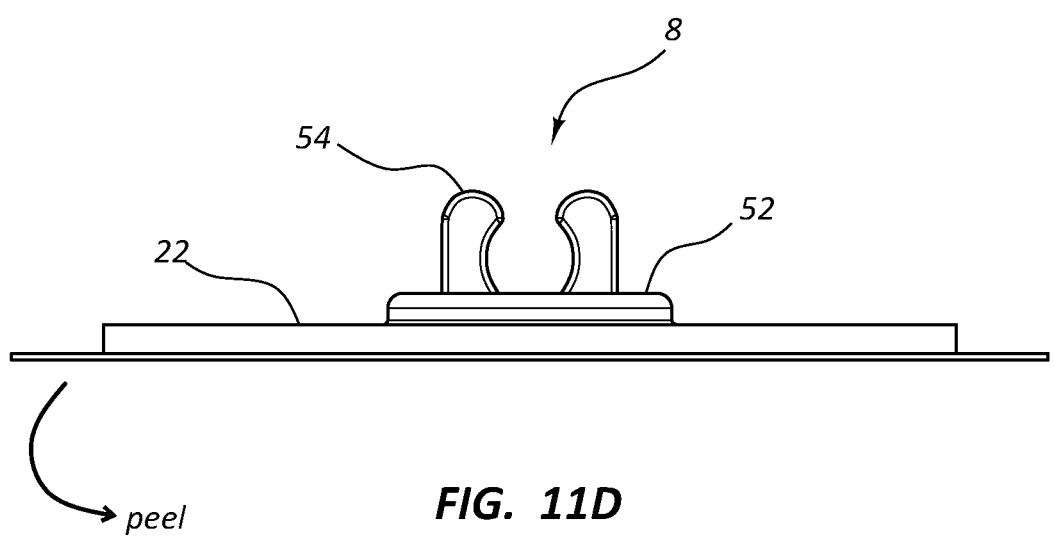
FIG. 11D shows a side view of the first securement device mounted on the adhesive pad in accordance with some embodiments.
Figure 11E:
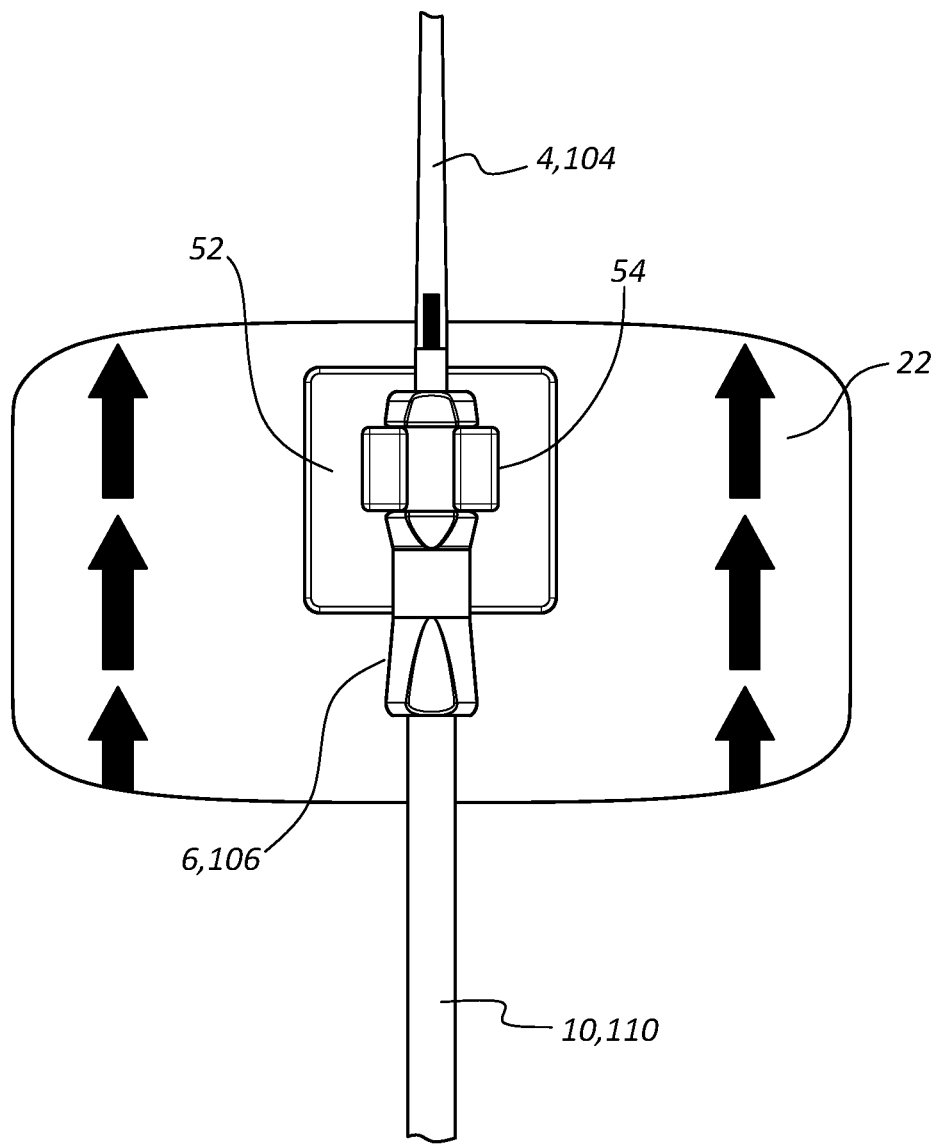
FIG. 11E shows a top view of the catheter of FIG. 1A secured in the first securement device including the adhesive pad in accordance with some embodiments.

FIGS. 1A, 6B, and 11A-11E show a securement device 8. Securement device 8 can include a base 52 and prongs 54 extending from the base, which prongs can fit over and sit within the recessed portion 5 of the junction 6 or the recessed portion 105 of the junction 106 as shown in FIGS. 4D and 9D. The base can include adhesive on the bottom thereof to attach the base 52 directly to a patient's clothes or skin or to attach the base to an adhesive pad or bandage 22 as shown in FIGS. 11C, 11D, and 11E. The base 52 can also be attached to the patient or a bandage by other means (e.g., a clamp, tie, wrap, hook and loop fastener, etc.). The securement device can be configured and sized to fit around an outer diameter of the junction/bifurcation to inhibit movement of the junction/bifurcation when the junction/bifurcation is held in the securement device. The junction 6 or 106 can attach to the securement device 8 by snapping in between the prongs 54. The prongs 54 can be flexible enough to expand to allow the junction 6 or 106 to be removably inserted and held therebetween, but provide a strong, secure hold on the junction 6 or 106 to prevent undesired movement. The prongs can be flexible enough to fit around and secure a variety of sizes and configurations of junctions 6 or 106 or other devices.

FIGS. 1B, 6A, and 12A-12C show a securement device 9. Securement device 9 can include wings or suture wing 66, a base 62, and barbs or posts 64 extending from the base. The wings/suture wing 66 is shown in more detail in FIGS. 10A, 10B, 10C, and 10D. The wings/suture wing can be removably attachable to the junction 6, 106, both, or other junctions or devices, wherein such junctions and devices can include a circumferentially recessed portion 5 or 105 about an outer diameter configured to accept or interlock with the suture wing 66. The suture wing can include a central passage or tunnel portion 74 formed by an arch region or U-shaped portion with an inner diameter sized to fit over and sit within the recessed portion 5 of the junction 6 or the recessed portion 105 of the junction 106 as shown in FIGS. 4D and 9D. The central passage or tunnel portion 74 can be able to flex or expand to allow the junction 6 or 106 to be removably inserted and held therebetween, but provide a strong, secure hold on the junction 6 or 106 to inhibit or prevent undesired movement of the junction when the catheter (e.g., PICC) is inserted in a pediatric patient such as a neonatal patient. The central passage or tunnel portion 74 can be flexible enough to fit around and secure a variety of sizes and configurations of junctions 6 or 106 or other devices.

Figure 10B:
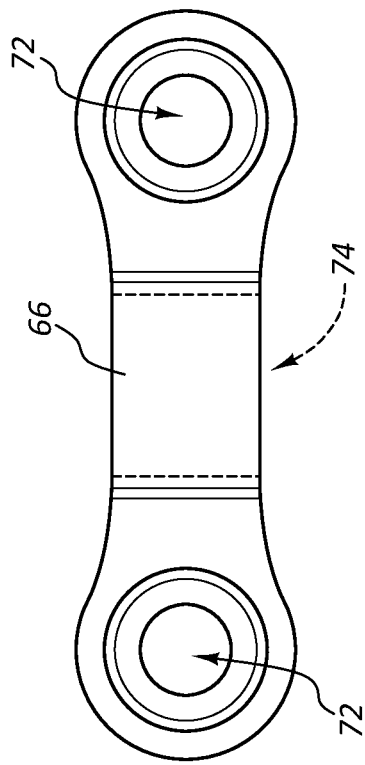
FIG. 10B shows a top view of the suture wing of FIG. 10A in accordance with some embodiments.
Figure 10D:
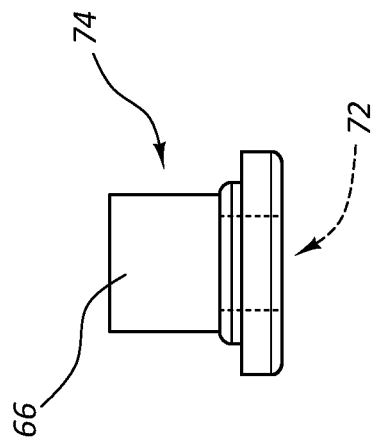
FIG. 10D shows an end view of the suture wing of FIG. 10A in accordance with some embodiments.
Figure 10A:
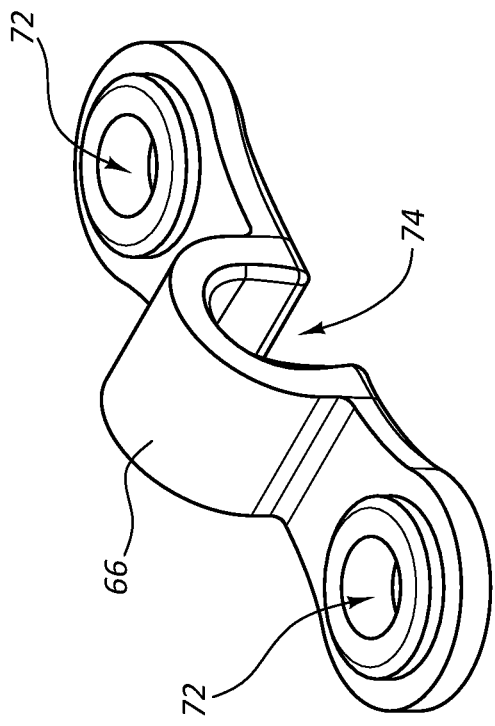
FIG. 10A shows a perspective view of a suture wing of the catheter of FIG. 1B or FIG. 6B in accordance with some embodiments.
Figure 10C:
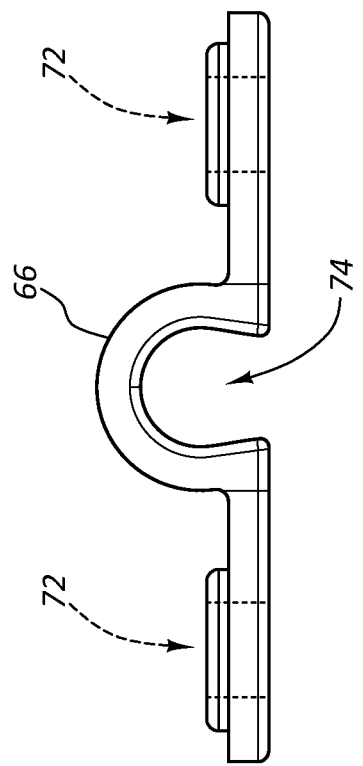
FIG. 10C shows a side view of the suture wing of FIG. 10A in accordance with some embodiments.
Figure 12A:
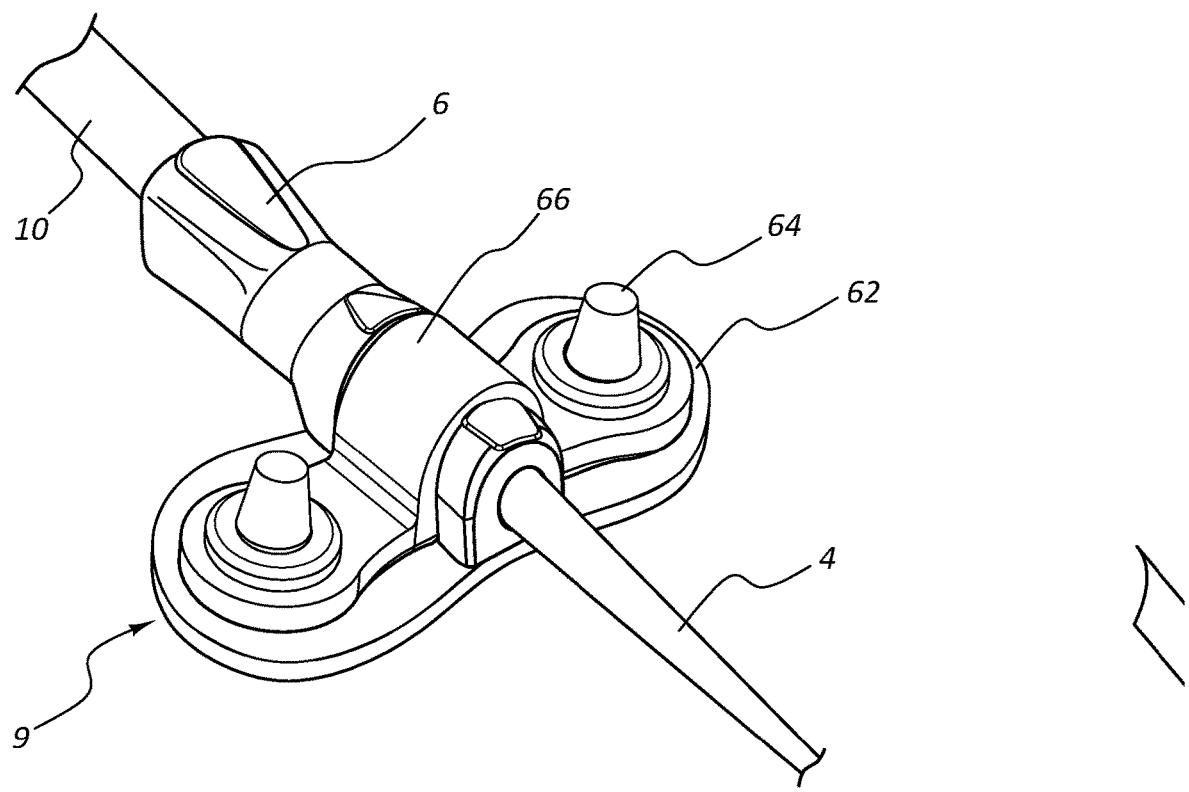
FIG. 12A shows a perspective view of the catheter of FIG. 1B secured with the suture wing in a second securement device in accordance with some embodiments.
Figure 12B:
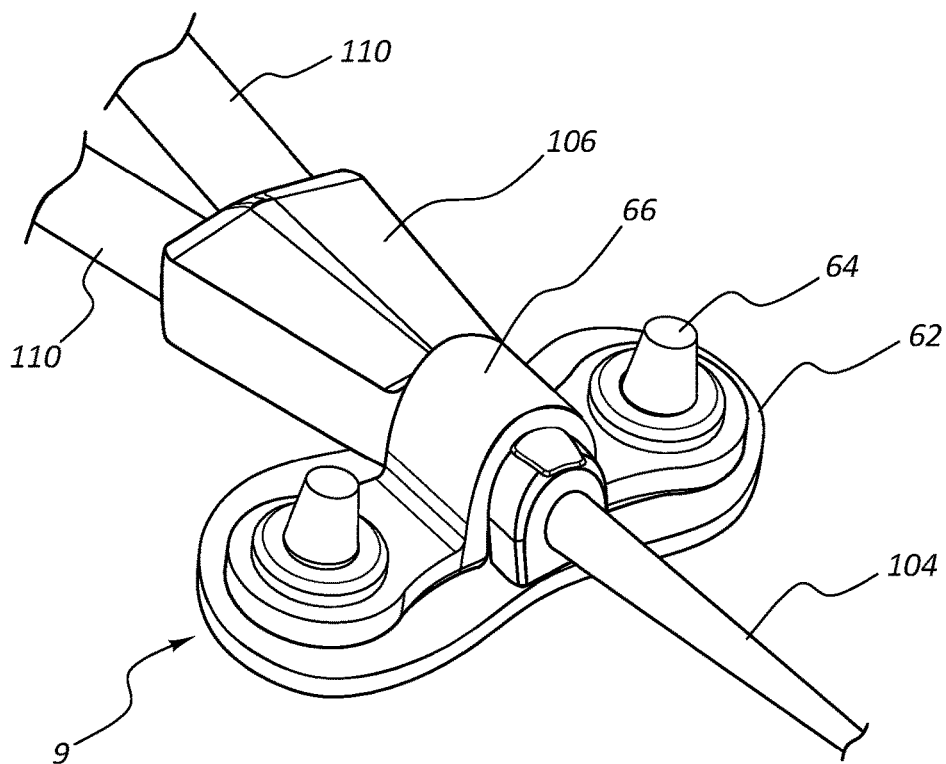
FIG. 12B shows a perspective view of the catheter of FIG. 6B secured with the suture wing in the second securement device in accordance with some embodiments.
Figure 12C:
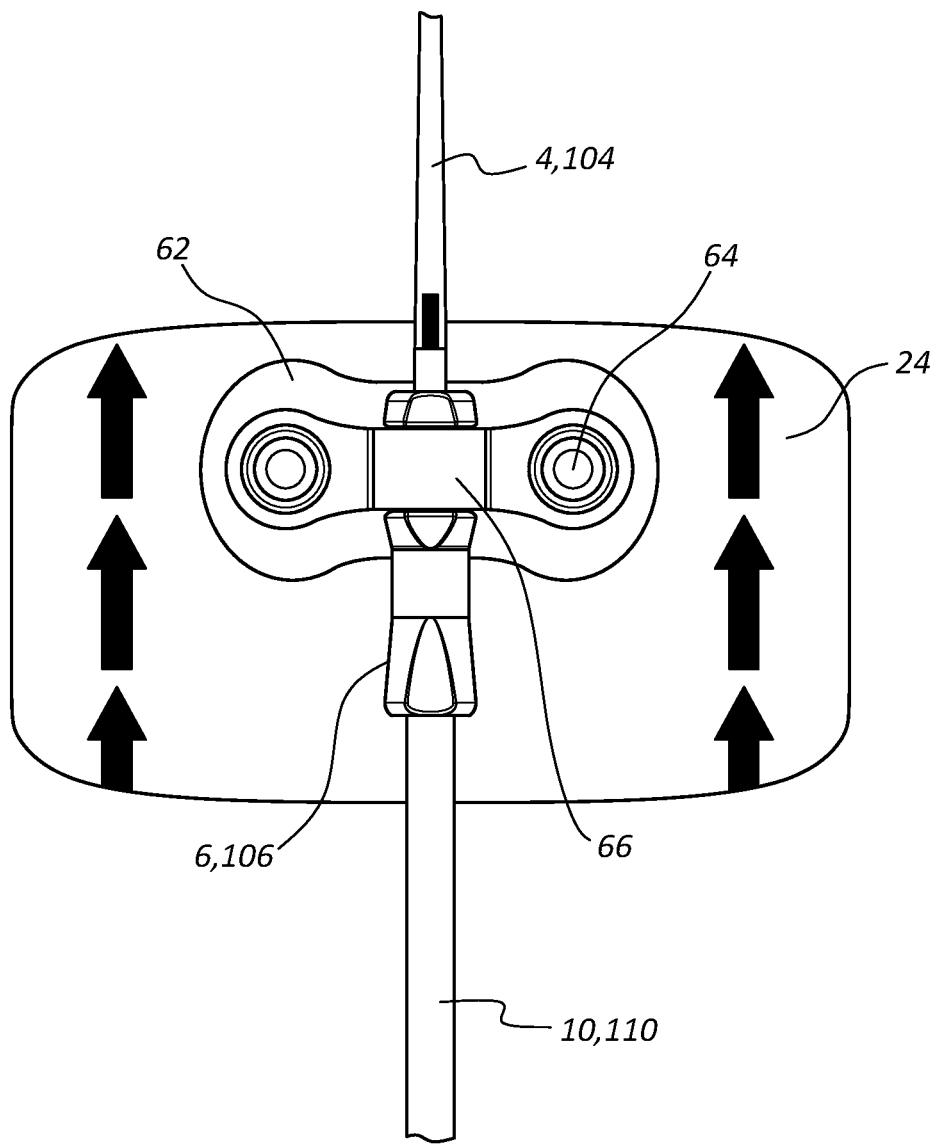
FIG. 12C shows a top view of the catheter of FIG. 1B secured with the suture wing in the second securement device including an adhesive pad in accordance with some embodiments.

The suture wing 66 can act as a securement device on its own. The suture wing 66 can include holes or openings 72 that can accept sutures or another structure to tie or hold the wings down and secure the suture wing 66 and junction or device held therein. The holes or openings 72 can be in the side wings or side extensions to either side of the arch region as shown in FIGS. 10A, 10B, and 10C. The holes or openings 72 can also be able to receive barbs 64 to hold the suture wing securely to the base 62 and thereby hold the junction 6 or 106 or another device therein. The barbs 64 can include an expanded diameter portion or barbed portion that allows the holes or openings to slide down the barbs to attach to the base, but prevent or resist the wings coming up off the barbs 64, i.e., the barbs can include a tapered portion that gives a slowly expanding diameter that the holes 72 can easily slip over on the way down the barb, but an abrupt edge (not tapered) on the lower end that makes it difficult for the wings to move back up the barbs 64 once snapped in place over them. The base 62 can include adhesive on the bottom thereof to attach the base 62 directly to a patient's clothes or skin or to attach the base to an adhesive pad or bandage 24 as shown in FIG. 12C. The base 62 can also be attached to the patient or a bandage by other means (e.g., a clamp, tie, wrap, hook and loop fastener, etc.).

Any portion of the securement device 8 or 9 (e.g., the suture wing 66 of the securement device 9) up to the entire securement device can be formed of polycarbonate or a replacement therefor having similar properties, such as a thermoplastic polyurethane having a greater ratio of hard to soft segments.

While only single and dual lumen catheters are provided as specific examples herein, other multiple lumen catheters might also be used with the inventive features herein (e.g., three-lumen or four-lumen catheters can include the same or similar features described herein).

The PICCs 2 and 102 can also include one or more extension legs 10, 110 that can be formed in a variety of sizes and shapes with a variety of materials (e.g., an aromatic polyether-based thermoplastic polyurethanes such as Tecothane™, for example, Tecothane™ 85A, or one or more other materials described herein). The extension legs 10, 110 can include one or more clamps 12 or 112 that can be used to close off the lumen(s) of the extension legs 10, 110. The clamp can be formed in a variety of different ways and of a variety of materials (e.g., polyoxymethylene or "acetal") and is not limited to the example shown in the figures. The extension legs 10, 110 can include one or more luers or luer connectors 14, 114 as shown in FIGS. 5A, 5B, and 5C to connect the extension legs to an injector, syringe, or other device to allow passage of liquid between the injector, syringe, or other device and the extension legs and catheter tube. The luers or luer connectors 14, 114 can have reduced dimensions for use with smaller patients, e.g., pediatric or neonatal patients. The wings or ridges of the luers or luer connectors can also be of reduced size. Such luers or luer connectors can be formed of polycarbonate or a replacement therefor having similar properties, such as a thermoplastic polyurethane having a greater ratio of hard to soft segments (Isoplast®).

The various catheters, devices, components, systems, etc. shown in the figures are sized to work exceptionally well for small PICCs used for pediatric or neonatal patients. There are significant challenges in manufacturing a catheter that is strong and reliable, but small enough for a neonatal patient. Finding sizes that work well and reduce the overall footprint of the catheter can be challenging.

The apparatuses, devices, systems, components, etc. described herein can be manufactured in a variety of ways, including using extrusion, a mold or cast, injection molding, 3D printing, welding, carving, other methods, and/or a combination of these. All or some materials used to make the apparatuses, devices, systems, components, etc. discussed above can be polymer materials, polyurethane, silicone, latex, PVC, HDPE, PTFE, ePTFE, metals, etc. Methods of manufacturing can include taking steps to form or combine components or features described in the order/arrangement shown or described herein.

While generally described herein in terms of PICC catheters and securement devices, the principles and design features described can also be used with different types of catheters and securement devices or other types of medical devices.

The catheters and securement devices and components thereof described herein can be used in a variety of methods. Methods of using the catheters and securement devices or any of their components can include any of the steps discussed herein, including steps of (1) providing or obtaining a catheterization system, catheter, and/or securement device (e.g., having some or all of the features described herein), (2) making/accessing an incision or opening in a patient's (e.g., a pediatric or neonatal patient) skin and/or a blood vessel, (3) navigating the catheter to a desired location in the body (e.g., placement of a PICC), (4) attaching a securement device to the catheter or a junction of the catheter (e.g., in any described herein), (5) attaching the securement device to the patient, (6) treating the patient, (7) infusing and/or extracting a fluid into or from a patient. These and other steps described herein can be performed in the order disclosed or in a different sequence, and steps can be omitted or added.

In view of the foregoing, a PICC is provided for pediatric patients including, in some embodiments, a catheter tube, one or more extension legs, and a junction coupling a proximal end of the catheter tube to the one or more extension legs. The catheter tube can include a tapered portion that extends from a proximal end of the catheter tube to a medial portion of the catheter tube. The tapered portion of the catheter tube can include a first outer diameter with a first wall thickness at the proximal end of the catheter tube and a second, smaller outer diameter with a second, thinner wall thickness at the medial portion of the catheter tube. The junction can include a circumferentially recessed portion about an outer diameter of the junction configured to interlock with a securement device to inhibit movement of the junction when the PICC is inserted in a pediatric patient such as a neonatal patient.

In such embodiments, the first wall thickness can be of a sufficient thickness to prevent breakage about the proximal end of the catheter tube when the PICC is handled or inserted in a neonatal patient in accordance with instructions for use packaged with the PICC.

In such embodiments, the tapered portion of the catheter tube can be up to about 10% of a total length of the catheter tube such as more than about 5% of the total length of the catheter tube and up to about 10% of the total length of the catheter.

In such embodiments, the catheter tube can include markings every centimeter along a length of the tapered portion of the catheter tube and markings every 2 mm or 2.5 mm along a 3-cm length of the catheter tube proximate the tapered portion to assist a medical practitioner in pull-back adjustments when positioning the catheter.

In such embodiments, the catheter tube can have a French size up to about 2 Fr distal to the tapered portion of the catheter tube.

In such embodiments, the catheter tube can include a thermoplastic polyurethane.

In such embodiments, the junction can include one or more tapered lumens configured to match lumen diameters of the one or more extension legs and the catheter tube in the junction. The catheter tube can be a single-lumen catheter tube, wherein the catheter tube can be configured for a flow rate up to about 5.0 mL/min. The catheter tube can alternatively be a dual-lumen catheter tube, wherein each lumen of the dual-lumen catheter tube can be configured for a flow rate up to about 1.5 mL/min.

Also provided herein is a catheterization system for treatment of pediatric patients including, in some embodiments, a PICC and a securement device. The PICC can include a catheter tube joined to one or more extension legs with a junction. The catheter tube can include a taper proximate the junction. The taper can transition the catheter tube in a proximal to distal direction from a first outer diameter and a first wall thickness to a second outer diameter smaller than the first outer diameter and a second wall thickness smaller than the first wall thickness. The securement device can be configured to fit around a recessed portion around an outer diameter of the junction to inhibit movement of the junction when the junction is held in the securement device.

In such embodiments, the taper can be configured to prevent the catheter tube from breaking at or proximate the junction.

In such embodiments, the first wall thickness can be at least three times as thick as the second wall thickness.

In such embodiments, the securement device can include a suture wing forming a U-shaped portion configured to sit in the recessed portion of the junction when the junction is held in the securement device.

In such embodiments, the suture wing can removably attach to the junction.

In such embodiments, the PICC is a dual-lumen catheter.

Also provided herein is a method for treatment of pediatric patients including, in some embodiments, obtaining a catheterization system, navigating a catheter of the catheterization system to a desired location in a patient's body, and securing the catheter in a securement device of the catheterization system. The catheterization system can include the foregoing catheter with the tapered catheter tube joined to the one or more extension legs with the junction. The catheterization system can further include the foregoing securement device configured to fit around the recessed portion of the outer diameter of the junction. Navigating the catheter of the catheterization system to the desired location in the patient's body can include accessing an opening in the patient's skin before navigating the catheter to the desired location in the patient's body. Securing the catheter in the securement device of the catheterization system can include attaching the securement device to the patient's skin and attaching the junction of the catheter to the securement device, thereby inhibiting movement of the junction when the junction is held in the securement device.

In such embodiments, the method can further include infusing a fluid into the patient, extracting a liquid from the patient, or both at different times.

The above apparatuses, devices, components, systems, assemblies, methods, etc. have generally been described as being applied to catheters and securement devices and their components; however, the principles described can be applied to a variety of other apparatuses, devices, components, systems, assemblies, methods, etc. Further, the features described in one embodiment herein can generally be combined with features described in other embodiments herein.

While the apparatuses, devices, components, systems, assemblies, methods, etc. of this invention can have been described in terms of particular variations and illustrative figures, it will be apparent to those skilled in the art that the invention is not so limited and that variations can be applied to other shelters, apparatuses, devices, components, systems, assemblies, methods, etc. For example, with respect to the methods, uses, and/or steps described herein variations can occur in the steps, uses, the sequence/order of steps, etc. described herein without departing from the concept, spirit, and scope of the invention, as defined by the claims. Additionally, certain of the steps can be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A peripherally inserted central catheter for a neonatal patient, comprising:
    a catheter tube sized for insertion into the neonatal patient, the catheter tube including:
        a tapered portion extending from a proximal end of the catheter tube to a medial portion of the catheter tube, the tapered portion including:
            a first outer diameter with a first wall thickness at the proximal end of the catheter tube;
            a second outer diameter with a second wall thickness at the medial portion of the catheter tube, wherein the second outer diameter is smaller than the first outer diameter, and wherein the second wall thickness is thinner than the first wall thickness; and
            a zero marking on an outer surface of the catheter tube indicating the beginning of the tapered portion; and
        a distal portion including a third outer diameter with a third wall thickness, wherein the third outer diameter is less than or equal to the second outer diameter, and wherein the third wall thickness is less than or equal to the second wall thickness;
    one or more extension legs; and
    a junction coupling the proximal end of the catheter tube to the one or more extension legs, the junction including a circumferentially recessed portion about an outer diameter of the junction configured to interlock with a securement device in a snap-fit arrangement to inhibit movement of the junction when the peripherally inserted central catheter is inserted in the neonatal patient.

2. The peripherally inserted central catheter of claim 1, wherein the first wall thickness is sufficiently thick to prevent breakage about the proximal end of the catheter tube when the peripherally inserted central catheter is handled or inserted in the neonatal patient in accordance with instructions for use of the peripherally inserted central catheter.

3. The peripherally inserted central catheter of claim 1, wherein the tapered portion of the catheter tube is up to about 10% of a total length of the catheter tube.

4. The peripherally inserted central catheter of claim 3, wherein the tapered portion of the catheter tube is more than about 5% of a total length of the catheter tube.

5. The peripherally inserted central catheter of claim 1, wherein the catheter tube includes markings every centimeter along a length of the tapered portion of the catheter tube and markings every 2 mm or 2.5 mm along a 3-cm length of the catheter tube proximate the tapered portion to assist a medical practitioner in pull-back adjustments when positioning the peripherally inserted central catheter.

6. The peripherally inserted central catheter of claim 5, wherein the markings along the length of the tapered portion include open or filled triangles, and the markings along the 3-cm length of the catheter tube include a combination of open or filled squares and circles.

7. The peripherally inserted central catheter of claim 1, wherein the catheter tube has a French size up to about 2 Fr distal to the tapered portion of the catheter tube.

8. The peripherally inserted central catheter of claim 1, wherein the catheter tube includes a thermoplastic polyurethane.

9. The peripherally inserted central catheter of claim 1, the junction includes one or more tapered lumens configured to match lumen diameters of the one or more extension legs and the catheter tube in the junction.

10. The peripherally inserted central catheter of claim 9, wherein the catheter tube is a single-lumen catheter tube.

11. The peripherally inserted central catheter of claim 10, wherein a lumen of the single-lumen catheter tube is configured for a flow rate up to about 5.0 mL/min.

12. The peripherally inserted central catheter of claim 9, wherein the catheter tube is a dual-lumen catheter tube.

13. The peripherally inserted central catheter of claim 12, wherein each lumen of the dual-lumen catheter tube is configured for a flow rate up to about 1.5 mL/min.

14. A catheterization system for treatment of neonatal patients, comprising:
    a peripherally inserted central catheter, comprising:
        a catheter tube sized for insertion into a neonatal patient, the catheter tube joined to one or more extension legs with a junction, the junction including a recessed diameter portion having a width, the catheter tube including:
            a taper proximate the junction, the taper transitioning the catheter tube from a first outer diameter and a first wall thickness to a second outer diameter smaller than the first outer diameter and a second wall thickness smaller than the first wall thickness in a proximal to distal direction, the catheter tube having a first marking to indicate a beginning of the taper and a second marking to indicate an end of the taper; and
            a distal portion including a third outer diameter with a third wall thickness, wherein the third outer diameter is less than or equal to the second outer diameter, and wherein the third wall thickness is less than or equal to the second wall thickness; and
    a securement device including a suture wing having a width matching the width of the recessed diameter portion, the suture wing including a portion designed for disposition in the recessed diameter portion of the junction to inhibit movement of the junction when the junction is held in the securement device.

15. The catheterization system of claim 14, wherein the taper is configured to prevent the catheter tube from breaking at or proximate the junction.

16. The catheterization system of claim 14, wherein the first wall thickness is at least three times as thick as the second wall thickness.

17. The catheterization system of claim 14, wherein the suture wing portion designed for disposition in the recessed diameter portion is a U-shaped portion.

18. The catheterization system of claim 17, wherein the suture wing removably attaches to the junction.

19. The catheterization system of claim 14, wherein the peripherally inserted central catheter is a dual-lumen catheter.

20. The catheterization system of claim 14, wherein the catheter tube includes markings every centimeter along a length of the taper beginning with the first marking, and wherein the catheter tube includes markings every 2 mm along a 3-cm length of the catheter tube distal to the tapered portion to assist a medical practitioner in initially inserting the catheter and in pull-back adjustments when positioning the catheter in the neonatal patient.

21. The catheterization system of claim 20, wherein the markings along the length of the taper include filled triangles, and the markings along the 3-cm length of the catheter tube include a combination of filled squares and circles.

22. A method, comprising:
   obtaining a catheterization system, the catheterization system comprising:
      a catheter comprising a catheter tube sized for insertion into a neonatal patient, the catheter tube joined to one or more extension legs with a junction, the junction including a recessed diameter portion having a length, the catheter tube including:
         a taper proximate the junction, the taper transitioning the catheter tube from a first outer diameter and a first wall thickness to a second outer diameter smaller than the first outer diameter and a second wall thickness smaller than the first wall thickness in a proximal to distal direction, the catheter tube having a first marking to indicate a beginning of the taper and a second marking to indicate an end of the taper; and
         a distal portion including a third outer diameter with a third wall thickness, wherein the third outer diameter is less than or equal to the second outer diameter, and wherein the third wall thickness is less than or equal to the second wall thickness; and
      a securement device including an interlock feature designed for a snap-fit arrangement with the recessed diameter portion of the junction to inhibit movement of the junction when the junction is held in the securement device, the interlock feature comprising a base including opposing prongs extending up from the base, each of the opposing prongs having a length substantially equivalent to the length of the recessed diameter portion;
   accessing an opening in a neonatal patient's skin;
   navigating the catheter to a desired location in a neonatal patient's body;
   attaching the securement device to the junction by inserting the recessed diameter portion into the interlock feature between the opposing prongs;
   attaching the securement device to the patient's skin; and
   infusing a fluid into the neonatal patient.

23. The method of claim 22, further comprising extracting a liquid from the neonatal patient.

24. The catheterization system of claim 22, wherein the opposing prongs are configured to expand to allow the junction to be inserted between the opposing prongs and securely hold the junction to inhibit movement of the junction.

* * * * *